(12) United States Patent
Matsuda et al.

(10) Patent No.: US 11,761,891 B2
(45) Date of Patent: Sep. 19, 2023

(54) RECEIVER, FIRE DETECTION SYSTEM, AND FIRE DETECTION METHOD

(71) Applicant: NEC Corporation, Tokyo (JP)

(72) Inventors: Yuma Matsuda, Tokyo (JP); Akihiro Tanaka, Tokyo (JP)

(73) Assignee: NEC CORPORATION, Tokyo (JP)

( * ) Notice: Subject to any disclaimer, the term of this patent is extended or adjusted under 35 U.S.C. 154(b) by 340 days.

(21) Appl. No.: 17/263,288

(22) PCT Filed: Jun. 6, 2019

(86) PCT No.: PCT/JP2019/022457
§ 371 (c)(1),
(2) Date: Jan. 26, 2021

(87) PCT Pub. No.: WO2020/026589
PCT Pub. Date: Feb. 6, 2020

(65) Prior Publication Data
US 2021/0215604 A1 Jul. 15, 2021

(30) Foreign Application Priority Data
Jul. 31, 2018 (JP) .............................. JP2018-144310

(51) Int. Cl.
*G01N 21/53* (2006.01)
*G01N 33/00* (2006.01)
*G08B 17/103* (2006.01)

(52) U.S. Cl.
CPC ......... *G01N 21/534* (2013.01); *G01N 33/004* (2013.01); *G01N 33/006* (2013.01); *G08B 17/103* (2013.01)

(58) Field of Classification Search
CPC .. G01N 21/534; G01N 33/004; G01N 33/006; G01N 21/314; G01N 21/31; G08B 17/103
(Continued)

(56) References Cited

U.S. PATENT DOCUMENTS 6,839,636 B1 * 1/2005 Sunshine ........... G01N 33/0032
702/30
7,335,885 B2 * 2/2008 Wong ...................... G01T 1/00
340/629

(Continued)

FOREIGN PATENT DOCUMENTS

CN 106448020 A 2/2017
JP S63-167242 A 7/1988
(Continued)

OTHER PUBLICATIONS

Japanese Office Communication for JP Application No. 2020-534082 dated Jun. 7, 2022 with English Translation.
(Continued)

*Primary Examiner* — Eric Blount
(74) *Attorney, Agent, or Firm* — Sughrue Mion, PLLC

(57) ABSTRACT

A receiver (10) according to the present disclosure includes: a detection unit (11) including a sensor configured to receive a first optical signal of a wavelength included in an absorption band of water molecules and a second optical signal of a wavelength included in an absorption band of carbon dioxide molecules, a signal processing unit (12) configured to calculate a water vapor concentration and a carbon dioxide concentration from changes of intensities of the first and second optical signals, and a determination unit (13) configured to determine whether or not there is a fire that is caused by alcohol combustion based on the water vapor concentration and the carbon dioxide concentration.

5 Claims, 17 Drawing Sheets

(58) Field of Classification Search
USPC .................................................. 340/628–630
See application file for complete search history.

(56) References Cited

U.S. PATENT DOCUMENTS

| | | | | |
|---|---|---|---|---|
| 2002/0075910 A1* | 6/2002 | Imaki | ................... | H01S 5/0687 |
| | | | | 372/50.23 |
| 2002/0152037 A1* | 10/2002 | Sunshine | ................ | H04L 67/12 |
| | | | | 702/23 |
| 2007/0114412 A1* | 5/2007 | Wong | ................. | G01N 21/0303 |
| | | | | 250/336.1 |
| 2013/0021612 A1 | 1/2013 | Okada | | |
| 2017/0166983 A1* | 6/2017 | Ritchie | ................ | A01H 6/4684 |
| 2019/0296519 A1* | 9/2019 | Kassi | ..................... | G01N 21/39 |

FOREIGN PATENT DOCUMENTS

| JP | H04-24797 A | | 1/1992 |
|---|---|---|---|
| JP | 2000-314700 A | | 11/2000 |
| JP | 2000314700 A | * | 11/2000 |
| JP | 2003-162778 A | | 6/2003 |
| JP | 2005-083876 A | | 3/2005 |
| JP | 2007-040891 A | | 2/2007 |
| JP | 2007-316765 A | | 12/2007 |
| JP | 2013-024728 A | | 2/2013 |
| JP | 2013-096810 A | | 5/2013 |
| JP | 2014-229193 A | | 12/2014 |

OTHER PUBLICATIONS

International Search Report for PCT Application No. PCT/JP2019/022457, dated Jul. 16, 2019.
Masahiko Sasaki et al., "Technology and Procurement of Deep Underground Tunnels", 21st Japan and Korea Construction Technology Seminar (2010), Japan.
Takaya Iseki, "Trace Gas Detection Technology using Near-irsfrared Semiconductor Laser", Journal of the Japan Society of Mechanical Engineers, vol. 107, No. 1022, p. 51 (2004), Japan.
Hayato Saito et al., "Measurement of atmospheric carbon dioxide by applying differential absorption spectroscopy in the near infrared region", 31st Laser Sensing Symposium, D-3 (2013), Japan.
Yonggang Chen et al., "Development of a Fire Detection System Using FT-IR Spectroscopy and Artificial Neural Networks" Fire Safety Science—Proceedings of the Sixth International Symposium, Jan. 2000, USA.

* cited by examiner

RECEIVER, FIRE DETECTION SYSTEM, AND FIRE DETECTION METHOD

This application is a National Stage Entry of PCT/JP2019/022457 filed on Jun. 6, 2019, which claims priority from Japanese Patent Application 2018-144310 filed on Jul. 31, 2018, the contents of all of which are incorporated herein by reference, in their entirety.

TECHNICAL FIELD

The present disclosure relates to a receiver, a fire detection system, and a fire detection method.

BACKGROUND ART

In recent years, the percentage of tunnel structures on expressways has been increasing. In 2010, in metropolitan expressways in Japan, the percentage of tunnel structures in sections of these expressways that are in service was 9.4%, whereas the percentage of tunnel structures in sections of these expressways that are under construction was 70% (Non-Patent Literature 1). If a disaster such as a fire occurs in a tunnel, the tunnel will be filled with smoke as it is a highly confined space. In the tunnel, it is difficult to perform evacuation and guidance for evacuation due to the possibility that people may inhale smoke and visibility may be poor. In order not to spread damage, evacuation and guidance for evacuation need to be started promptly. In order to start this evacuation and the guidance for evacuation promptly, it is absolutely necessary to detect a fire promptly and accurately and to issue an alert. Further, in urban areas, lands are used intensively by using elevated structures and underground spaces, which make it difficult to secure sites for providing new expressways. In order to solve this problem, it is expected that a deep underground, which is deeper than the conventional underground, will be used. In deep underground facilities as well, prompt and accurate fire detection and issuance of an alert are absolutely necessary due to a reason similar to that in the tunnel structures.

Blaze detection has been mainly used as a fire detection method in tunnels in Japan. In this method, infrared light is detected from a blaze. Therefore, a fire can be detected only after occurrence of a blaze, as a result of which an initial response may be delayed and thus damage may spread. In countries other than Japan, for example, in European countries, a temperature detector and a smoke detector have been introduced and have been used to detect a fire. There is a problem, however, that a reaction speed is low and it is difficult to distinguish environmental changes due to exhaust gas or the like of automobiles or trucks from a fire. A fire detection method capable of distinguishing a fire from other environmental changes and detecting a fire promptly with few errors in reports and few losses of reports has been required.

Under the above circumstances, Patent Literature 1 discloses a method of performing a fire detection using an optical gas detection system in which an optical signal is emitted to a measurement target space and the concentration of the target gas in the measurement target space and the transmittance are measured in view of a change in an intensity of the optical signal after the propagation thereof. According to this method, it is possible to monitor a wide area by one detection system. This system issues an alert for a fire when the concentration of the target gas exceeds a threshold and the transmittance is below the threshold. Patent Literature 2 discloses a system for determining whether there is a fire using light emitting means, light receiving means, and fire determination means. The light emitting means emits at least two types of wavelength light beams with different emission wavelengths. The light receiving means receives attenuated light due to smoke of a plurality of wavelength light beams emitted from the light emitting means. The fire determination means determines that there is a fire when time changes of light receiving outputs for the respective different wavelengths obtained from the light receiving means are compared and it is determined that there is a mutual relationship between predetermined time changes as a result of the comparison. By providing the fire determination means, it is possible to capture the difference in the amount of light with time due to smoke of different wavelength light beams that occurs only in the event of a fire and more accurately determine whether there is a fire. Patent Literature 3 discloses a method of determining whether smoke is non-fire smoke or fire smoke from a ratio between wavelengths of a dimming coefficient of each wavelength obtained based on light receiving outputs of a plurality of wavelengths or a ratio between wavelengths of a dimming degree of each wavelength. According to this method, it is possible to discern the size of the smoke particles, thereby enabling discriminating of fire smoke from non-fire smoke. In Patent Literature 1 to 3, it is determined whether there is a fire using dimming due to smoke.

The optical gas detection system uses a characteristic that it absorbs light having a wavelength that is unique for each substance. Typically, there are two methods of calculating a gas concentration. The first method is a method of detecting gas by modulating a wavelength using a light source having a narrow wavelength band that outputs a wavelength in the vicinity of an absorption wavelength. One example of this method is a Wavelength Modulation Spectroscopy (WMS) disclosed in Non-Patent Literature 2. The second method is a method of calculating a gas concentration from a known spectrum intensity using a light source having a wide wavelength band. One example of this method is Differential Optical Absorption Spectroscopy (DOAS) disclosed in Non-Patent Literature 3.

CITATION LIST

Patent Literature

[Patent Literature 1] Japanese Unexamined Patent Application Publication No. 2005-83876
[Patent Literature 2] Japanese Unexamined Patent Application Publication No. S63-167242
[Patent Literature 3] Japanese Unexamined Patent Application Publication No. H04-024797

Non-Patent Literature

[Non-Patent Literature 1] Masahiko Sasaki et al., "Technology and Procurement for Deep Underground Road Tunnel", 21st Japan and Korea Construction Technology Seminar (2010)
[Non-Patent Literature 2] Takaya Iseki, "Trace Gas Detection Technology using Near-infrared Semiconductor Laser", Journal of the Japan Society of Mechanical Engineers, Vol. 107, No. 1022, p. 51 (2004)
[Non-Patent Literature 3] Hayato Saito et al., "Absorption Measurement of Carbon Dioxide in Atmosphere by applying Differential Absorption Spectroscopy in Near-infrared Region", 31st Laser Sensing Symposium, D-3 (2013)

[Non-Patent Literature 4] Yonggang Chen et al., "Development of a Fire Detection System Using FT-IR Spectroscopy and Artificial Neural Networks", FIRE SAFETY SCIENCE-Proceedings of Sixth International Symposium, pp. 791-802

SUMMARY OF INVENTION

Technical Problem

Combustion of alcohol such as ethanol produces only small amounts of smoke and carbon monoxide. Therefore, it is impossible to detect a fire according to methods disclosed in Patent Literature 1, 2, and 3 in which transmittance is used as an index. As an example, consider biofuels. The amount of world biofuel production increased six or more times in ten years from 2000 to 2010. In many countries, due to concern for the environment, they have used biofuels that emit smaller amounts of smoke and carbon monoxide than conventional fuels do mixed with a fuel for automobiles. Some automobiles use 100% bioethanol or biodiesel, which is a biofuel. There is a problem in Patent Literature 1, 2, and 3 that it is impossible to accurately detect a fire in these automobiles.

An object of the present disclosure is to provide a receiver, a fire detection system, and a fire detection method capable of dealing with scenarios of a wider range and carrying out accurate fire detection in a wide-area sensor that propagates optical signals and monitors fire situations.

Solution to Problem

A receiver according to a first aspect of the present disclosure includes: a detection unit including a sensor configured to receive a first optical signal of a wavelength included in an absorption band of water molecules and a second optical signal of a wavelength included in an absorption band of carbon dioxide molecules; a signal processing unit configured to calculate a water vapor concentration and a carbon dioxide concentration from changes in intensities of the first and second optical signals; and a determination unit configured to determine whether or not there is a fire that is caused by alcohol combustion based on the water vapor concentration and the carbon dioxide concentration.

A fire detection system according to a second aspect of the present disclosure includes: a receiver including a detection unit including a sensor configured to receive a first optical signal of a wavelength included in an absorption band of water molecules and a second optical signal of a wavelength included in an absorption band of carbon dioxide molecules, a signal processing unit configured to calculate a water vapor concentration and a carbon dioxide concentration from changes in intensities of the first and second optical signals, and a determination unit configured to determine whether or not there is a fire that is caused by alcohol combustion based on the water vapor concentration and the carbon dioxide concentration; and a transmitter including at least one laser light source configured to transmit each of the first and second optical signals to the receiver.

A fire detection method according to a third aspect of the present disclosure includes: receiving a first optical signal of a wavelength included in an absorption band of water molecules and a second optical signal of a wavelength included in an absorption band of carbon dioxide molecules; calculating a water vapor concentration and a carbon dioxide concentration from changes in intensities of the first and second optical signals; and determining whether or not there is a fire based on the changes in the water vapor concentration and the carbon dioxide concentration.

Advantageous Effects of Invention

According to the fire detection system of the present disclosure, it is possible to provide a receiver, a fire detection system, and a fire detection method capable of dealing with scenarios of a wider range and carrying out accurate fire detection in a wide-area sensor that propagates optical signals and monitors fire situations.

DESCRIPTION OF EMBODIMENTS

First Example Embodiment

Figure 17:
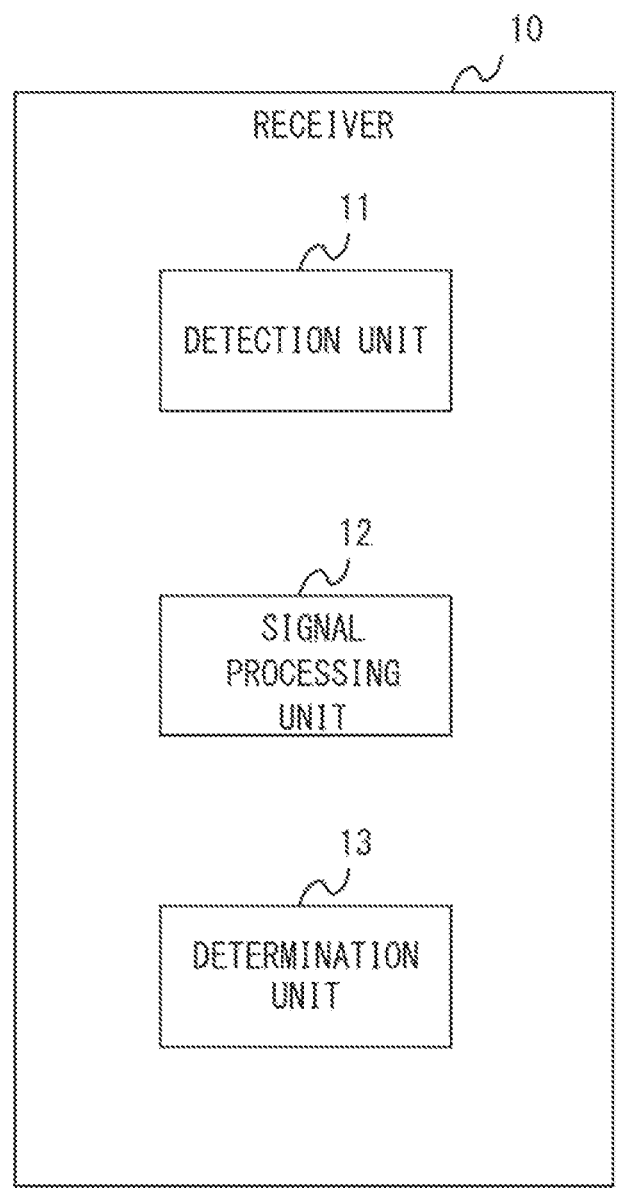
FIG. 17 is a configuration diagram of a receiver according to a first example embodiment.

Hereinafter, with reference to the drawings, a first example embodiment according to the present disclosure will be described. With reference to FIG. 17, a configuration example of a receiver included in a fire detection system according to a first example embodiment will be described. The fire detection system may also be used as a wide-area sensor that propagates optical signals and monitors fire situations. A receiver (10) may be a computer apparatus operated by a processor executing a program stored in a memory. The receiver (10) includes a detection unit (11), a signal processing unit (12), and a determination unit (13). The detection unit (11), the signal processing unit (12), and the determination unit (13) may be software or modules whose processing is executed by a processor executing the program stored in the memory. Alternatively, the detection unit (11), the signal processing unit (12), and the determination unit (13) may be hardware such as circuits or chips.

The detection unit (11) includes a sensor configured to receive a first optical signal of a wavelength included in an absorption band of water molecules and a second optical signal of a wavelength included in an absorption band of carbon dioxide molecules. The sensor configured to receive the first optical signal may be different from the sensor that receives the second optical signal. Alternatively, one sensor may receive the first optical signal and the second optical signal. The absorption band indicates absorption that occurs in one wavelength range due to light or the like hitting a substance.

The signal processing unit (12) calculates a water vapor concentration and a carbon dioxide concentration using changes in intensities of the first and second optical signals. The intensity of the optical signal may be, for example, amplitude or an amount of light of the optical signal.

The determination unit (13) determines whether or not there is a fire that is caused by alcohol combustion based on the water vapor concentration and the carbon dioxide concentration. The determination unit (13) may determine, when the water vapor concentration and the carbon dioxide concentration each indicate a value larger than a predetermined reference value or a threshold, for example, that there is a fire that has occurred due to alcohol combustion.

As described above, the receiver (10) is able to determine whether or not there is a fire based on the water vapor concentration and the carbon dioxide concentration. Accordingly, the receiver (10) is able to determine whether or not there is a fire that is caused by alcohol combustion which does not generate much carbon monoxide and smoke.

Second Example Embodiment

Figure 1:
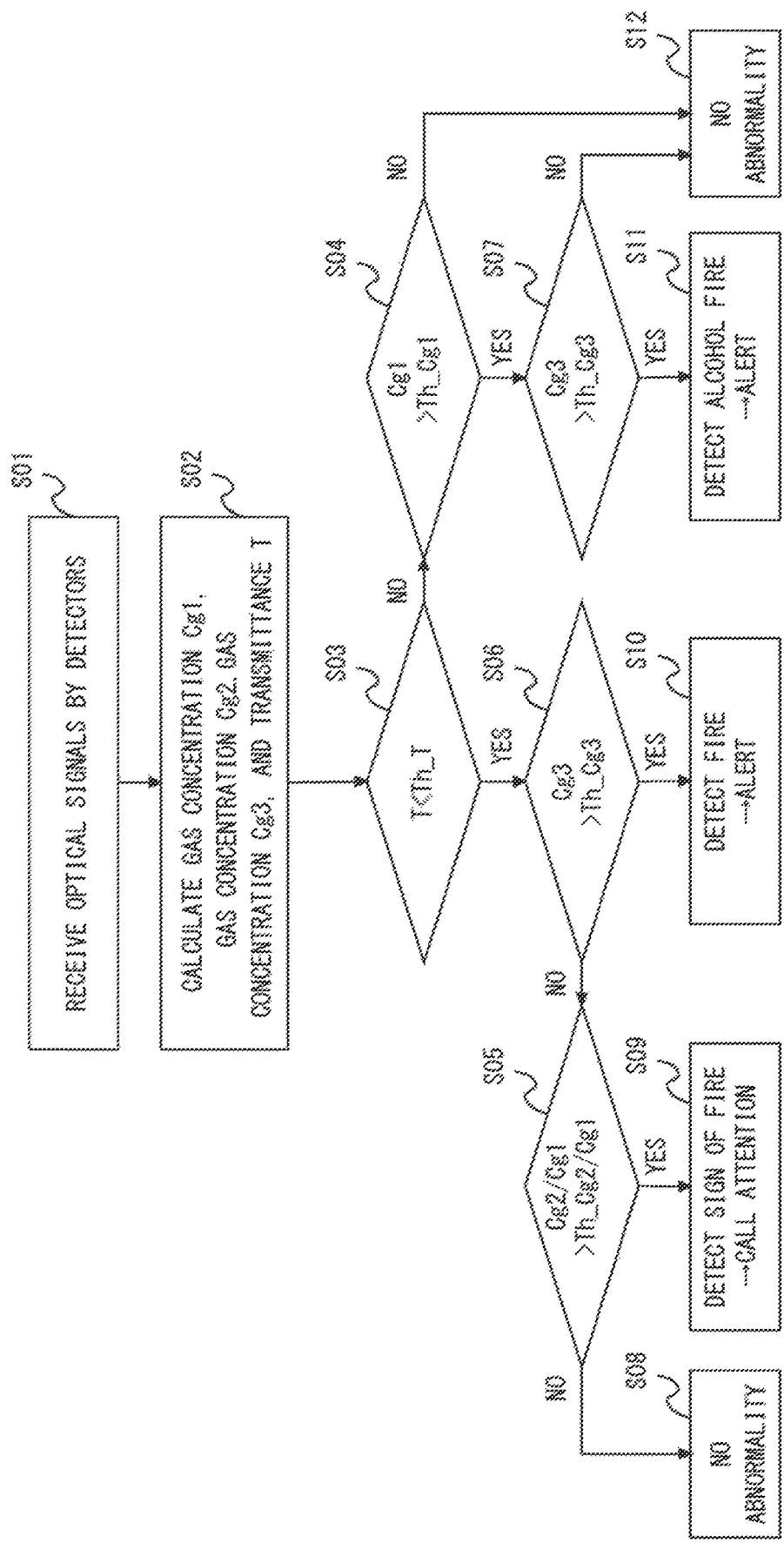
FIG. 1 is a diagram showing a flow of processing of determining a progress of a fire according to a second example embodiment.
Figure 2:
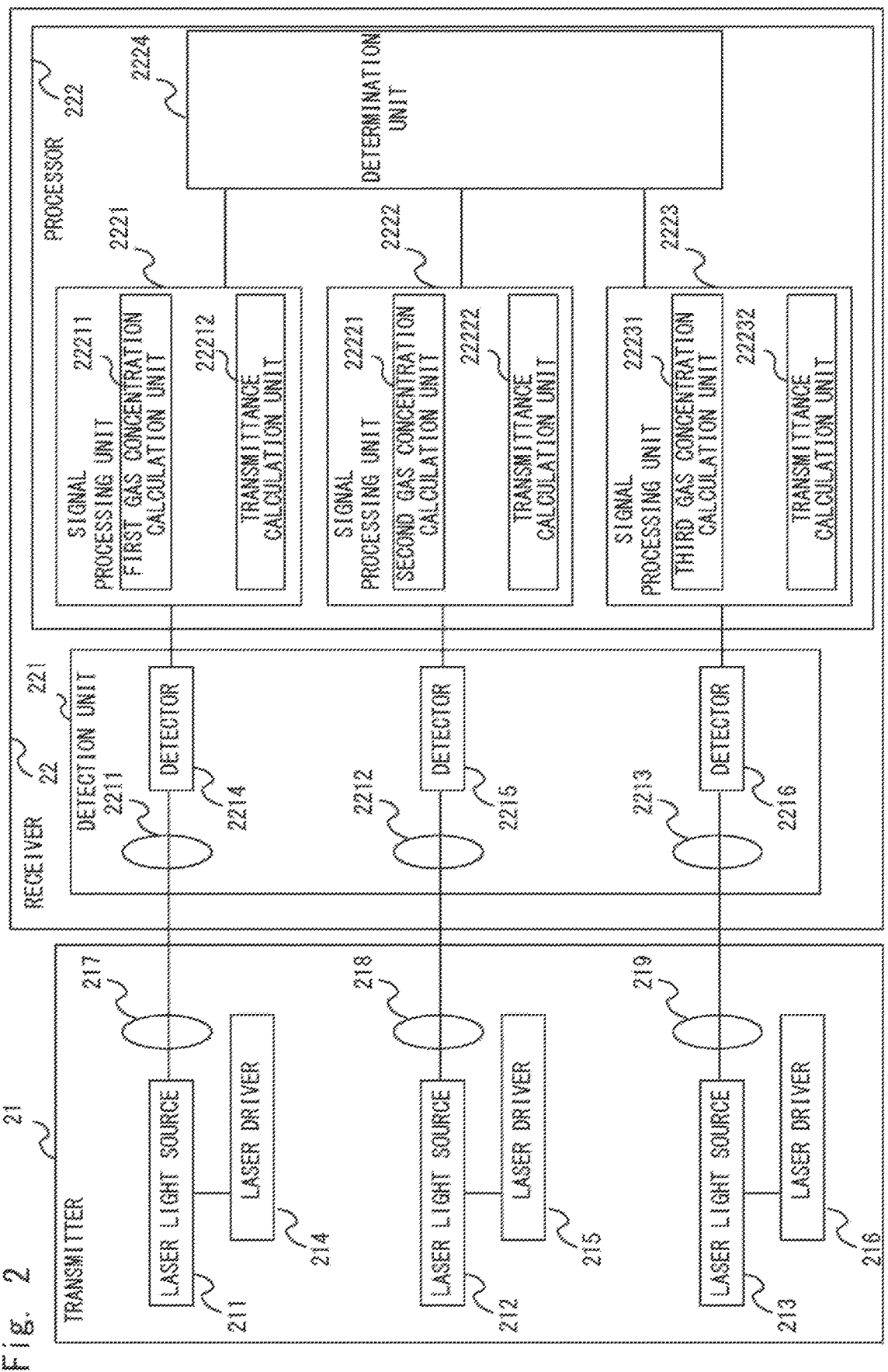
FIG. 2 is a configuration diagram of a fire detection system according to the second example embodiment.
Figure 3:
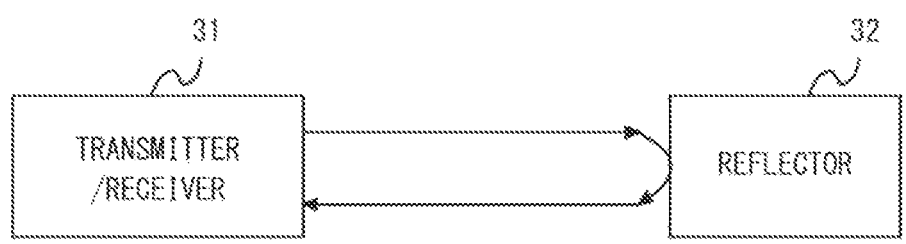
FIG. 3 is a diagram showing a transmitter/receiver in which a transmitter and a receiver are integrally formed according to the second example embodiment.

With reference to FIGS. 1, 2, and 3, a second example embodiment of the present disclosure will be described.

Configuration of Example Embodiment

FIG. 2 is a block diagram showing a configuration of a fire detection system according to this example embodiment. A transmitter (21) includes laser light sources (211, 212, and 213), laser drivers (214, 215, and 216), and condensers (217, 218, and 219). The three laser light sources (211, 212, and 213) output three optical signals. The three condensers (217, 218, and 219) respectively convert the optical signals output from the laser light sources (211, 212, and 213) into quasi-parallel light beams. Further, the three condensers (217, 218, and 219) transmit the optical signals converted into the quasi-parallel light beams to a receiver (22).

The receiver (22) includes a detection unit (221), signal processing units (2221, 2222, and 2223), and a determination unit (2224). The signal processing units (2221, 2222, and 2223) and the determination unit (2224) may be software or modules whose processing is executed by a processor (222) executing a program stored in a memory. Alternatively, the signal processing units (2221, 2222, and 2223) and the determination unit (2224) may be hardware such as circuits or chips.

The processor (222) loads software (computer program) from a memory and performs processing described using a flowchart or the like in the following description. The processor (222) may be, for example, a microprocessor, a Micro Processing Unit (MPU), or a Central Processing Unit (CPU). The processor (222) may include a plurality of processors.

The memory is composed of a combination of a volatile memory and a non-volatile memory. The memory may include a storage located apart from the processor (222). In this case, the processor (222) may access the memory via an I/O interface (not shown). The memory is used to store software or software modules. The processor (222) loads these software or software modules from the memory and executes them.

The detection unit (221) condenses the three respective received optical signals using three condensers (2211, 2212, and 2213). Three detectors (2214, 2215, and 2216) receive the respective optical signals condensed in the condensers (2211, 2212, and 2213) and convert the received optical signals into electric signals. The detectors (2214, 2215, and 2216) may be software or modules whose processing is executed by the processor (222) executing a program stored in a memory. Alternatively, the detectors (2214, 2215, and 2216) may be hardware such as circuits or chips. Further, the detectors (2214, 2215, and 2216) may be software or modules whose processing is executed by a processor other than the processor (222) executing a program stored in a memory.

The signal processing units (2221, 2222, and 2223) respectively include gas concentration calculation units (22211, 22221, and 22231) and transmittance calculation units (22212, 22222, and 22232). The gas concentration calculation units (22211, 22221, and 22231) calculate the gas concentration using the electric signals generated in the detectors (2214, 2215, and 2216). The transmittance calculation units (22212, 22222, and 22232) calculate the transmittance using the electric signals generated in the detectors (2214, 2215, and 2216). The transmittance is a rate of decrease of the optical signals from a state in which there is no smoke whose intensity is in a wavelength range around the absorption peak. The determination unit (2224) determines a progress of a fire based on the gas concentration and the transmittance that have been calculated. The transmittance is similarly reduced by smoke in any optical signal used in this example embodiment. Therefore, the transmittance used in the determination unit (2224) may be any one of the three values calculated in the transmittance calculation units (22212, 22222, and 22232).

Operations of Example Embodiment

Next, operations regarding the transmitter (21) and the receiver (22) will be described. The laser driver (214) controls a drive current and a temperature of an optical signal output from the laser light source (211). The laser light source (211) outputs an optical signal with a wavelength $\lambda 1$ μm. The condenser (217) converts the optical signal output from the laser light source (211) into a quasi-parallel light beam. The optical signal converted into the quasi-parallel light beam propagates through the measurement target space and is transmitted to the receiver (22).

The condenser (2211) condenses the received optical signal and outputs the condensed optical signal to the detector (2214). The detector (2214) receives the optical signal and converts the received optical signal into an electric signal. The detector (2214) outputs the electric signal to the signal processing unit (2221).

The first gas concentration calculation unit (22211) and the transmittance calculation unit (22212) calculate the average carbon dioxide (CO2) concentration and the average transmittance in the wavelength of λ1 μm in the section between the transmitter (21) and the receiver (22) from the change in the intensity of the optical signal.

The laser driver (215) controls a drive current and a temperature of the optical signal output from the laser light source (212). The laser light source (212) outputs an optical signal with a wavelength λ2 μm. The condenser (218) converts the optical signal output from the laser light source (212) into a quasi-parallel light beam. The optical signal converted into the quasi-parallel light beam propagates through the measurement target space and is transmitted to the receiver (22).

The condenser (2212) condenses the received optical signal and outputs the condensed optical signal to the detector (2215). The detector (2215) receives the optical signal and converts the received optical signal into an electric signal. The detector (2215) outputs the electric signal to the signal processing unit (2222).

The second gas concentration calculation unit (22221) and the transmittance calculation unit (22222) calculate the average carbon monoxide (CO) concentration and the average transmittance in the wavelength of λ2 μm in the section between the transmitter (21) and the receiver (22) from the change in the intensity of the optical signal.

The laser driver (216) controls a drive current and a temperature of the optical signal output from the laser light source (213). The laser light source (213) outputs an optical signal with a wavelength λ3 μm. The condenser (219) converts the optical signal output from the laser light source (213) into a quasi-parallel light beam. The optical signal converted into the quasi-parallel light beam propagates through the measurement target space and is transmitted to the receiver (22).

The condenser (2213) condenses the received optical signal and outputs the condensed optical signal to the detector (2216). The detector (2216) receives the optical signal and converts the received optical signal into an electric signal. The detector (2216) outputs the electric signal to the signal processing unit (2223).

The third gas concentration calculation unit (22231) and the transmittance calculation unit (22232) calculate an average water vapor (H2O) concentration and an average transmittance in the wavelength of λ3 μm in the section between the transmitter (21) and the receiver (22) from the change in the intensity of the optical signal. The symbol λ1 denotes a wavelength included in an absorption band of CO2 molecules, λ2 denotes a wavelength included in an absorption band of CO molecules, and λ3 denotes a wavelength included in an absorption band of H2O molecules.

Referring next to a flowchart shown in FIG. 1, a method in which the receiver 22 determines a progress of a fire using the gas concentration and the transmittance that have been calculated by the aforementioned operation will be described. First, the detectors (2214, 2215, and 2216) receive optical signals (Step S01). Next, the gas concentration calculation unit (22211) calculates a concentration Cg1 of gas (CO2) based on the optical signal received by the detector (2214) (Step S02). Likewise, the gas concentration calculation units (22221 and 22231) calculate a concentration Cg2 of gas (CO) based on the optical signal received by the detector (2215) and calculates a concentration Cg3 of gas (H2O) based on the optical signal received by the detector (2216) (Step S02). Further, at least one of the transmittance calculation units (22212, 22222, and 22232) calculates a transmittance T from the optical signals (Step S02). The amount of decrease in the transmittance of an optical signal having a shorter wavelength is large since this signal is easily scattered. Therefore, the transmittance calculation unit (22212) may calculate the transmittance T using the optical signal of λ1 whose wavelength is the shortest among the three optical signals.

Next, the determination unit (2224) compares the calculated transmittance T with a threshold Th_T that has been preliminarily set (Step S03). When the transmittance is higher than the threshold, the determination unit (2224) determines that there is no smoke generated due to a fire. In this case, it is estimated that there is no fire or a fire due to alcohol or the like is occurring. In order to determine whether there is no fire or a fire due to alcohol or the like is occurring, the determination unit (2224) compares the gas concentration Cg1 with a threshold Th_Cg1 (Step S04) and the gas concentration Cg3 with a threshold Th_Cg3 (Step S07). When both of them exceed the thresholds, the determination unit (2224) determines that there is a fire due to alcohol combustion and issues an alert (Step S11). When one of them is below the threshold, the determination unit (2224) determines that there is no abnormality (Step S12).

When the transmittance T is below the threshold Th_T in Step S03, the determination unit (2224) compares the gas concentration Cg3 with the threshold Th_Cg3 (Step S06). The determination unit (2224) uses water vapor as an index for determining whether or not a normal fire is occurring since water vapor (H2O) is generated by a normal fire. A normal fire is, for example, a fire other than a fire due to alcohol combustion. Therefore, the determination unit (2224) may use carbon dioxide (CO2), which is generated by a normal fire, just as water vapor is, as an index for determining whether or not a normal fire is occurring. When the gas concentration Cg3 exceeds the threshold, the determination unit (2224) determines that it is a normal fire and issues an alert (Step S10).

When the gas concentration Cg3 is below the threshold in Step S06, the determination unit (2224) compares a gas concentration ratio Cg2/Cg1 with a threshold Th_Cg2/Cg1 (Step S05). As disclosed in Non-Patent Literature 4 etc., before a fire occurs, a large amount of carbon monoxide (CO) is generated but only a little amount of carbon dioxide (CO2) is generated. That is, before a fire occurs, the ratio of the concentration of carbon monoxide (CO) to the concentration of carbon dioxide (CO2) increases. Therefore, when Cg2/Cg1 exceeds the threshold, the determination unit (2224) determines that it is a sign of a fire indicating that a normal fire is about to occur and calls attention for a fire (Step S09). When Cg2/Cg1 is below the threshold, the determination unit (2224) determines that there is no abnormality (Step S08).

Figure 10:
FIG. 10 is a schematic view of a change in transmittance over time in the event of a normal fire and a non-fire.
Figure 11:
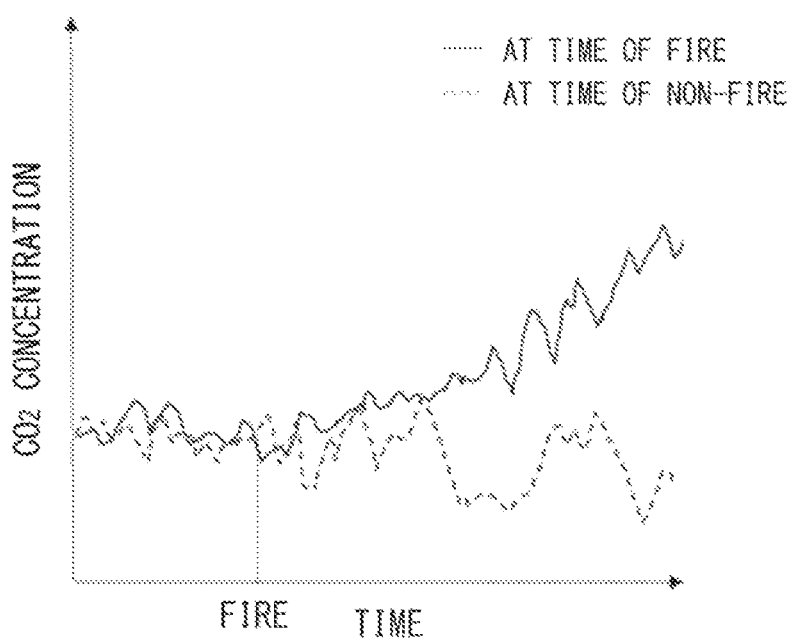
FIG. 11 is a schematic view of a change in CO2 concentration over time in the event of a fire and a non-fire.
Figure 12:
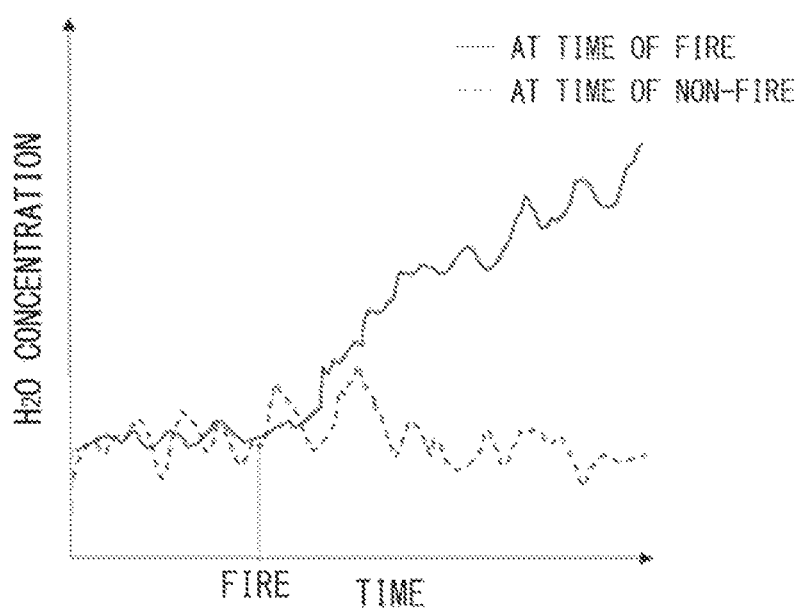
FIG. 12 is a schematic view of a change in H2O concentration over time in the event of a fire and a non-fire.
Figure 13:
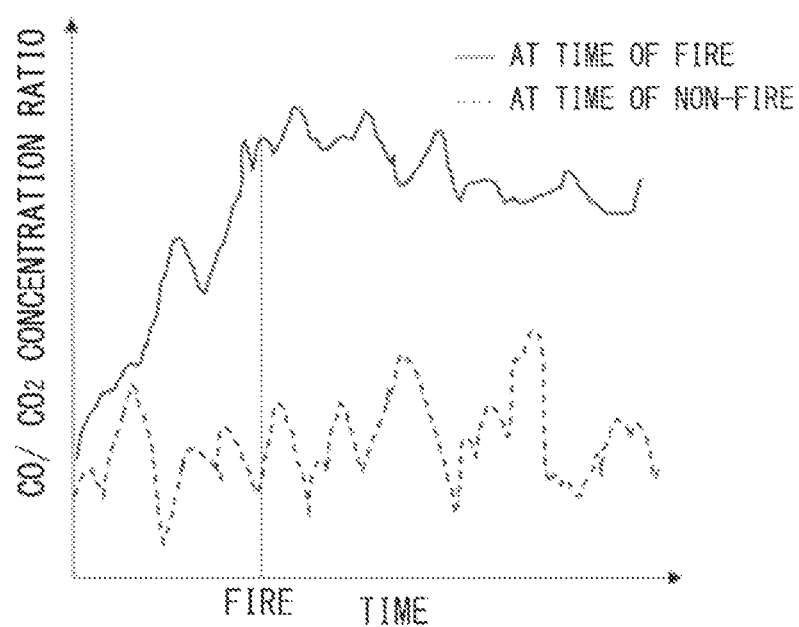
FIG. 13 is a schematic view of a change in a CO/CO2 concentration ratio over time in the event of a fire and a non-fire.
Figure 15:
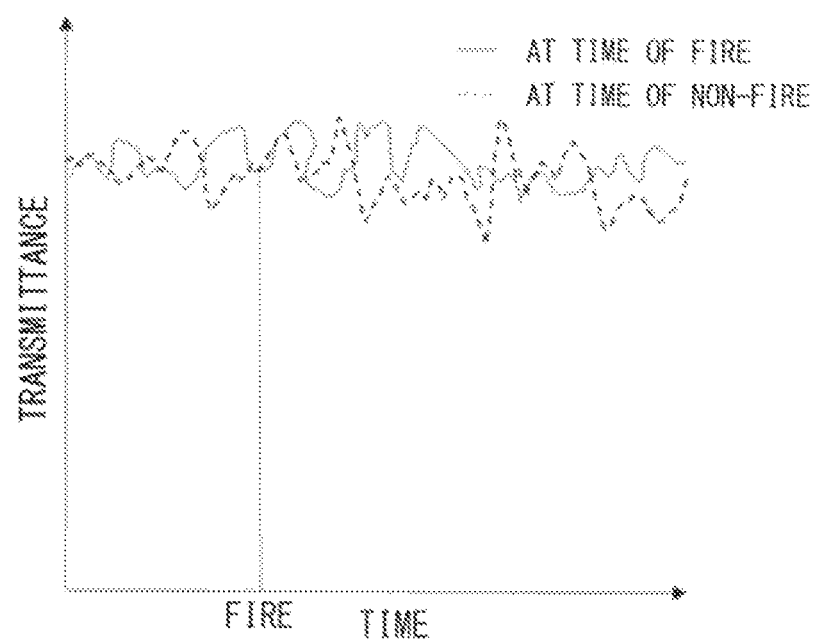
FIG. 15 is a schematic view of a change in the transmittance over time in the event of an alcohol fire and a non-fire.

FIG. 10 shows a schematic view of a change in the transmittance over time in the event of a normal fire and a non-fire. Further, FIG. 11 shows a schematic view of a change in the CO2 concentration over time in the event of a fire and a non-fire. Further, FIG. 12 shows a schematic view of a change in the H2O concentration over time in the event of a fire and a non-fire. Further, FIG. 13 shows a schematic view of a change in the CO/CO2 concentration ratio over time in the event of a fire and a non-fire. Further, FIG. 15 shows a schematic view of a change in the transmittance over time in the event of an alcohol fire and a non-fire.

Compared to the case in the event of a non-fire, in the event of a normal fire, the transmittance is decreased and the gas concentration is increased. When it is determined that there is a fire in both the change in the gas concentration and the change in the transmittance, the determination unit (2224) determines that a fire is occurring and issues an alert. As shown in FIG. 13, the rate of rise of the CO/CO2 concentration ratio is higher than those of other gases. When it has been determined, by using the above results, that there is a fire in both the change in the CO/CO2 concentration ratio and the change in the transmittance, the determination unit (2224) determines that the current state is a smoked state and calls attention for a fire. As shown in FIG. 15, in the event of an alcohol fire, the transmittance is not reduced. Therefore, when the transmittance is not reduced, the determination unit (2224) determines that there is an alcohol fire when it has been determined that a fire is occurring in both the change in the concentration of carbon dioxide and the change in the concentration of water vapor, both of which being generated in the event of an alcohol fire.

Effects of Example Embodiment

According to this example embodiment, the following two effects may be obtained. The first effect is that it is possible to deal with scenarios of a wider range in a wide-area sensor that propagates optical signals and monitors fire situations. A typical wide-area sensor detects a fire using smoke and carbon monoxide. Therefore, the typical wide-area sensor cannot accurately detect a fire using changes in the smoke and the carbon monoxide concentration in combustion of alcohol or the like where smoke and carbon monoxide are not generated in the event of a fire. In this example embodiment, both the change in the concentration of carbon dioxide and the change in the concentration of water vapor that are produced also in combustion of alcohol or the like are used as references, whereby the determination unit (2224) is able to perform strong detection for other environmental changes in a broad scenario.

The second effect is that it is possible to rapidly detect a normal fire in a wide-area sensor that propagates optical signals and monitors fire situations. In this example embodiment, the concentration ratio of carbon monoxide to carbon dioxide that is increased before occurrence of a blaze and the reduction in the transmittance due to smoke are combined with each other, whereby it is possible to capture a sign of the occurrence of a blaze before occurrence thereof.

Note that the contents of this example embodiment are not limited to the aforementioned description. In the aforementioned description, the determination unit (2224) evaluates, as an index of the determination, whether the transmittance is below the threshold. Alternatively, the determination unit (2224) may evaluate whether the smoke concentration Cs calculated based on the following expression exceeds the threshold.

$$I_s = I_o \times e^{-CsD} \quad (1)$$

Here, Io denotes an intensity of the optical signal output from the transmitter (21), Is denotes an intensity of the optical signal received by the receiver (22), and D denotes a distance between the transmitter (21) and the receiver (22).

Further, the example in which the transmitter (21) and the receiver (22) are separately used has been described in the aforementioned description, a transmitter/receiver (31) in which a transmitter and a receiver are integrally formed may be used, as shown in FIG. 3. The optical signal output from the transmitter/receiver (31) may be reflected in the direction of the transmitter/receiver (31) using a reflector (32) and the reflected optical signal may be received by the transmitter/receiver (31). According to this configuration, the number of devices that require power feeding can be limited to one and the number of devices that require anti-explosion measures may be reduced. At this time, the optical signal output from the transmitter/receiver (31) may be reflected a plurality of times and the reflected optical signal may be received by the transmitter/receiver (31), and the propagation distance may thus be increased. According to this configuration, the degree of accuracy of the measurement can be improved.

Further, while the example in which the signal processing unit is divided into three parts has been described in the aforementioned description, two of the three parts may be formed as one signal processing unit or all the three parts may be formed as one signal processing unit.

Further, in the aforementioned description, as an index for judging the sign of a normal fire, it is evaluated whether or not the concentration ratio of carbon monoxide (CO) with respect to carbon dioxide (CO2) exceeds the threshold. Alternatively, it may be evaluated whether the concentration of carbon monoxide (CO) exceeds the threshold instead of calculating the ratio. According to this configuration, the processing may be simplified.

Further, while the example in which the three transmittances are calculated and used based on the three optical signals has been described in the aforementioned description, the three transmittances may be averaged or two of the three transmittances may be averaged to improve the accuracy. Alternatively, the system may be simplified using one of the three transmittances. Further, a laser light source may be newly introduced and the transmittance may be calculated based on the output optical signal.

Further, while the example in which laser light sources are used as the three light sources has been described in the aforementioned description, wide-band light sources such as Light Emitting Diodes (LEDs) may instead be used. The gas concentration may be calculated using DOAS in accordance therewith.

Third Example Embodiment

Figure 4:
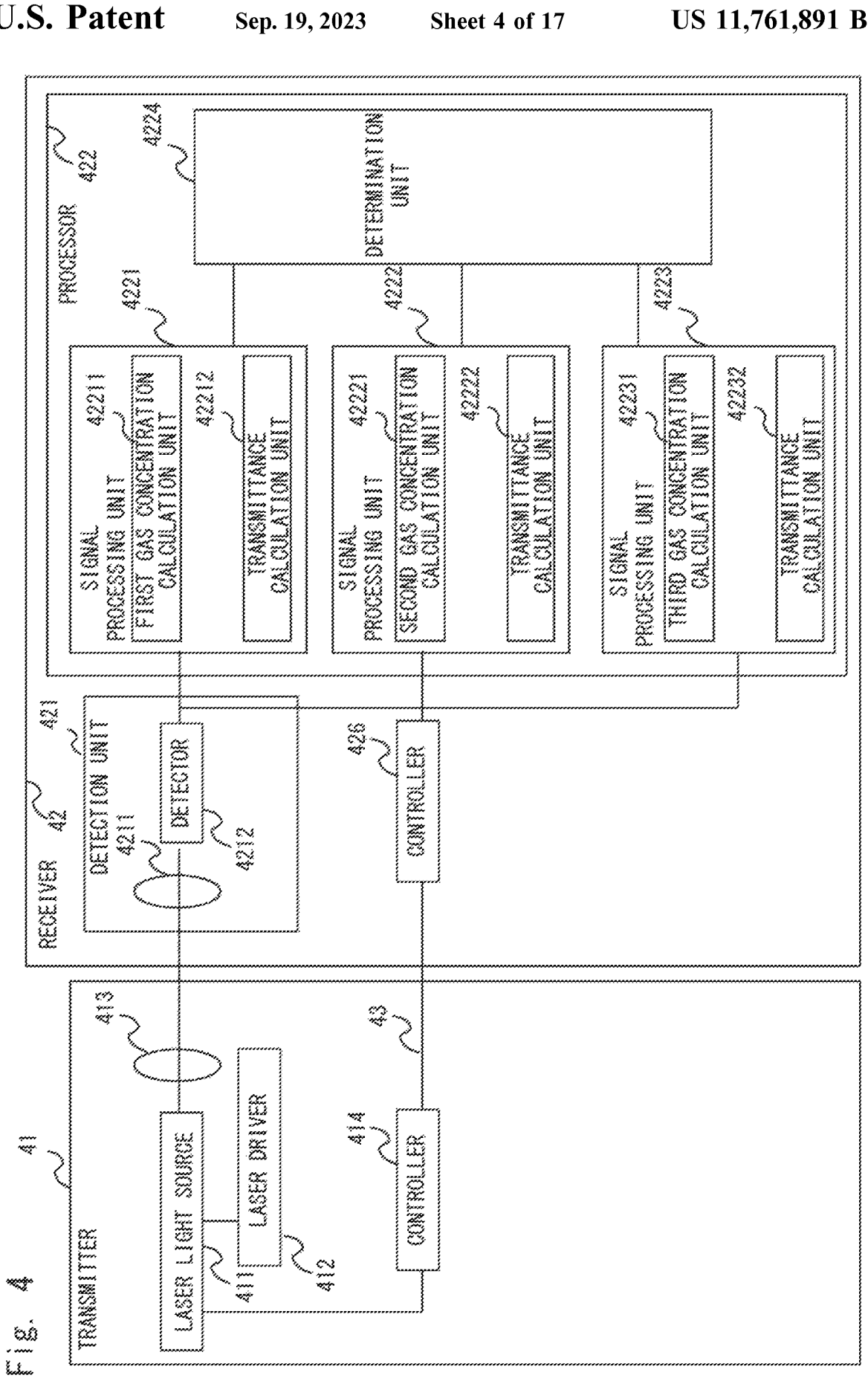
FIG. 4 is a configuration diagram of a fire detection system according to a third example embodiment.
Figure 5:
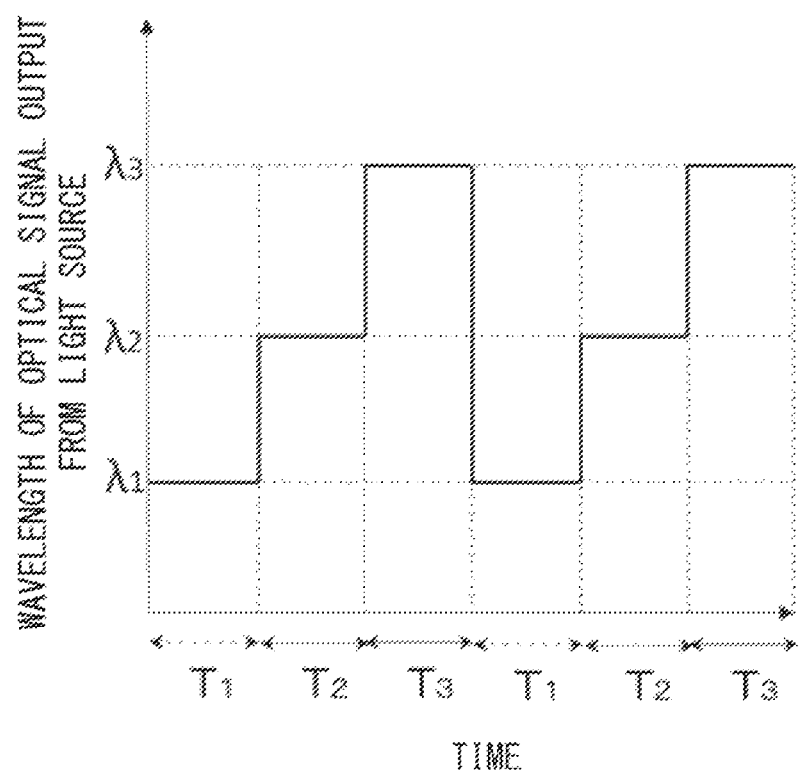
FIG. 5 is a diagram showing a relationship between a wavelength and time of an optical signal output from a laser light source according to the third example embodiment.

Referring next to FIGS. 4 and 5, a third example embodiment will be described. In the second example embodiment, the concentrations of the three types of gas and the transmittances are calculated using the three light sources and the progress of the fire has been determined based on them. In this example embodiment, the output wavelength of one light source is switched at regular time intervals, the concentrations of the three types of gas and the transmittances are calculated, and a fire, a normal fire sign, or a non-fire are determined.

Configuration of Example Embodiment

FIG. 4 shows a block diagram showing a configuration of a fire detection system according to this example embodiment. A transmitter (41) includes a laser light source (411), a laser driver (412), a controller (414), and a condenser (413). The laser light source (411) outputs an optical signal. The condenser (413) converts the optical signal output from the laser light source (411) into a quasi-parallel light beam. Further, the condenser (413) transmits the optical signal converted into the quasi-parallel light beam to a receiver (42).

The receiver (42) includes a detection unit (421), signal processing units (4221, 4222, and 4223), a determination unit (4224), and a controller (426). The signal processing units (4221, 4222, and 4223), the determination unit (4224), and the controller (426) may be software or modules whose processing is executed by a processor (422) executing a program stored in a memory. Alternatively, the signal processing units (4221, 4222, and 4223), the determination unit (4224), and the controller (426) may be hardware such as circuits or chips.

The detection unit (421) condenses the received optical signal using a condenser (4211). A detector (4212) receives the optical signal condensed in the condenser (4211) and converts the received optical signal into an electric signal. The detector (4212) may be software or a module whose processing is executed by the processor (422) executing a program stored in a memory. Alternatively, the detector (4212) may be hardware such as a circuit or a chip. Further, the detector (4212) may be software or a module whose processing is executed by a processor other than the processor (422) executing a program stored in a memory.

The signal processing units (4221, 4222, and 4223) respectively include gas concentration calculation units (42211, 42221, and 42231) and transmittance calculation units (42212, 42222, and 42232). The gas concentration calculation units (42211, 42221, and 42231) calculate the gas concentrations using the electric signal generated in the detector (4212). The transmittance calculation units (42212, 42222, and 42232) calculate the transmittances using the electric signal generated in the detector (4212). The transmittance is a rate of decrease of the optical signal from the state in which there is no smoke whose intensity is in a wavelength range around the absorption peak. The time in the controller (414) and that in the controller (426) are synchronized with each other. The controller (414) transmits a switch signal to the controller (426) at the timing of switching the wavelength of the optical signal output from the laser light source (411). Upon receiving the switch signal, the controller (426) changes the output destination of the electric signal output from the detector (4212). A wired cable (43) connects the controller (414) and the controller (426). The determination unit (4224) determines the progress of the fire from the gas concentrations and the transmittances that have been calculated. Since the transmittance is similarly reduced by smoke in any one of the optical signals that are used in this example embodiment, the transmittance used in the determination unit (4224) may be any one of the three values calculated in the transmittance calculation units (42212, 42222, and 42232).

Operations of Example Embodiment

Referring next to FIG. 5, a relationship between the wavelength of the optical signal output from the laser light source and time will be described. When the time is a period T1, the controller (414) causes the laser light source (411) whose drive current and temperature have been controlled by the laser driver (412) to output an optical signal with a wavelength $\lambda 1$ µm. The condenser (413) converts the optical signal output from the laser light source (411) into a quasi-parallel light beam. The optical signal converted into the quasi-parallel light beam propagates through the measurement target space and is transmitted to the receiver (42).

The condenser (4211) condenses the received optical signal and outputs the condensed optical signal to the detector (4212). The detector (4212) receives the optical signal and converts the received optical signal into an electric signal. The detector (4212) outputs the electric signal to the signal processing unit (4221).

The first gas concentration calculation unit (42211) and the transmittance calculation unit (42212) calculate an average carbon dioxide (CO2) concentration and an average transmittance in the wavelength of $\lambda 1$ µm in the section between the transmitter (41) and the receiver (42) from the change in the intensity of the optical signal.

When the time is a period T2, the controller (414) causes the laser light source (411) whose drive current and temperature have been controlled by the laser driver (412) to output an optical signal with a wavelength $\lambda 2$ µm. The condenser (413) converts the optical signal output from the laser light source (411) into a quasi-parallel light beam. The optical signal converted into the quasi-parallel light beam propagates through the measurement target space and is transmitted to the receiver (42).

The condenser (4211) condenses the received optical signal and outputs the condensed optical signal to the detector (4212). The detector (4212) receives the optical signal and converts the received optical signal into an electric signal. The detector (4212) outputs the electric signal to the signal processing unit (4222).

The second gas concentration calculation unit (42221) and the transmittance calculation unit (42222) calculate an average carbon monoxide (CO) concentration and an average transmittance in the wavelength of $\lambda 2$ µm in the section between the transmitter (41) and the receiver (42) from the change in the intensity of the optical signal.

When the time is a period T3, the controller (414) causes the laser light source (411) whose drive current and temperature have been controlled by the laser driver (412) to output an optical signal with a wavelength $\lambda 3$ µm. The condenser (413) converts the optical signal output from the laser light source (411) into a quasi-parallel light beam. The optical signal converted into the quasi-parallel light beam propagates through the measurement target space and is transmitted to the receiver (42).

The condenser (4211) condenses the received optical signal and outputs the condensed optical signal to the detector (4212). The detector (4212) receives the optical signal and converts the received optical signal into an electric signal. The detector (4212) outputs the electric signal to the signal processing unit (4223).

The third gas concentration calculation unit (42231) and the transmittance calculation unit (42232) calculate an average water vapor (H2O) concentration and an average transmittance in the wavelength of $\lambda 3$ µm in the section between the transmitter (41) and the receiver (42) from the change in the intensity of the optical signal.

The controller (414) and the controller (426) switch T1, T2, and T3 at regular time intervals and are synchronized with each other via the wired cable (43). The symbol $\lambda 1$ denotes a wavelength included in an absorption band of CO2 molecules, $\lambda 2$ denotes a wavelength included in an absorption band of CO molecules, and $\lambda 3$ denotes a wavelength included in an absorption band of H2O molecules.

FIG. 10 shows a schematic view of a change in the transmittance over time in the event of a normal fire and a non-fire. Further, FIG. 11 shows a schematic view of a change in the CO2 concentration over time in the event of a fire and a non-fire. Further, FIG. 12 shows a schematic view of a change in the H2O concentration over time in the event of a fire and a non-fire. Further, FIG. 13 shows a schematic view of a change in the CO/CO2 concentration ratio over time in the event of a fire and a non-fire. Further, FIG. 15 shows a schematic view of a change in the transmittance over time in the event of an alcohol fire and a non-fire.

Compared to the case in the event of a non-fire, in the event of a normal fire, the transmittance is decreased and the gas concentration is increased. When it has been determined that there is a fire in both the change in the gas concentration and the change in the transmittance, the determination unit (4224) determines that a fire is occurring and issues an alert. As shown in FIG. 13, the rate of rise of the CO/CO2 concentration ratio is higher than those of other gases. When it has been determined, by using the above results, that there is a fire in both the change in the CO/CO2 concentration ratio and the change in the transmittance, the determination unit (4224) determines that the current state is a smoked state, and calls attention for a fire. As shown in FIG. 15, in the event of an alcohol fire, the transmittance is not reduced. Therefore, when the transmittance is not reduced, the determination unit (4224) determines that an alcohol fire is occurring when it is determined that a fire is occurring from both the change in the carbon dioxide concentration and the change in the water vapor concentration, which are generated also when an alcohol fire occurs.

Effects of Example Embodiment

According to this example embodiment, besides the effects described in the second example embodiment, the following effects may be obtained. The transmitter (41) helps to reduce the number of laser light sources and reduce the cost. When three laser light sources are used, the cost typically increases greatly. According to this example embodiment, the number of laser light sources can be limited to one, whereby it is possible to reduce the cost compared to the case in which three laser light sources are used.

Note that the contents of this example embodiment are not limited to the aforementioned description. In the aforementioned description, the determination unit (4224) evaluates, as an index of the determination, whether the transmittance is below the threshold. Alternatively, the determination unit (4224) may evaluate whether the smoke concentration Cs calculated based on the following expression exceeds the threshold.

$$I_s = I_o \times e^{-CsD} \quad (1)$$

Here, Io denotes an intensity of the optical signal output from the transmitter (41), Is denotes an intensity of the optical signal received by the receiver (42), and D denotes a distance between the transmitter (41) and the receiver (42).

Further, while the example in which the transmitter (41) and the receiver (42) are separately used has been described in the aforementioned description, the transmitter/receiver (31) in which the transmitter and the receiver are integrally formed may instead be used, as shown in FIG. 3. The optical signal output from the transmitter/receiver (31) may be reflected in a direction of the transmitter/receiver (31) using the reflector (32) and may be received by the transmitter/receiver (31). According to this configuration, the number of devices that require power feeding can be limited to one, the number of devices that require anti-explosion measures may be reduced, there is no need to synchronize the controllers, and the wired cable may be removed.

Further, the wired cable for synchronization of the controller (414) and the controller (426) may be changed to a wireless connection. According to this configuration, the wired cable may be removed. At this time, the optical signal output from the transmitter/receiver (31) may be reflected a plurality of times and the reflected optical signal may be received by the transmitter/receiver (31), and the propagation distance may thus be increased. According to this configuration, the degree of accuracy of the measurement can be improved.

Further, while the example in which the signal processing unit is divided into three parts has been described in the aforementioned description, two of the three parts may be formed as one signal processing unit or all the three parts may be formed as one signal processing unit.

Further, in the aforementioned description, it is evaluated whether the concentration ratio of carbon monoxide to carbon dioxide exceeds a threshold as an index for judging the sign of a normal fire. Alternatively, it may be evaluated whether the concentration of carbon monoxide exceeds a threshold instead of calculating the ratio. According to this configuration, the processing may be simplified.

Further, while the example in which the three transmittances are calculated and used based on the three optical signals has been described in the aforementioned description, the three transmittances may be averaged or two of the three transmittances may be averaged to improve the accuracy. Alternatively, the system may be simplified by using one of the three transmittances. Further alternatively, a new light source may be introduced and the transmittance may be calculated based on the output optical signal.

Fourth Example Embodiment

Figure 6:
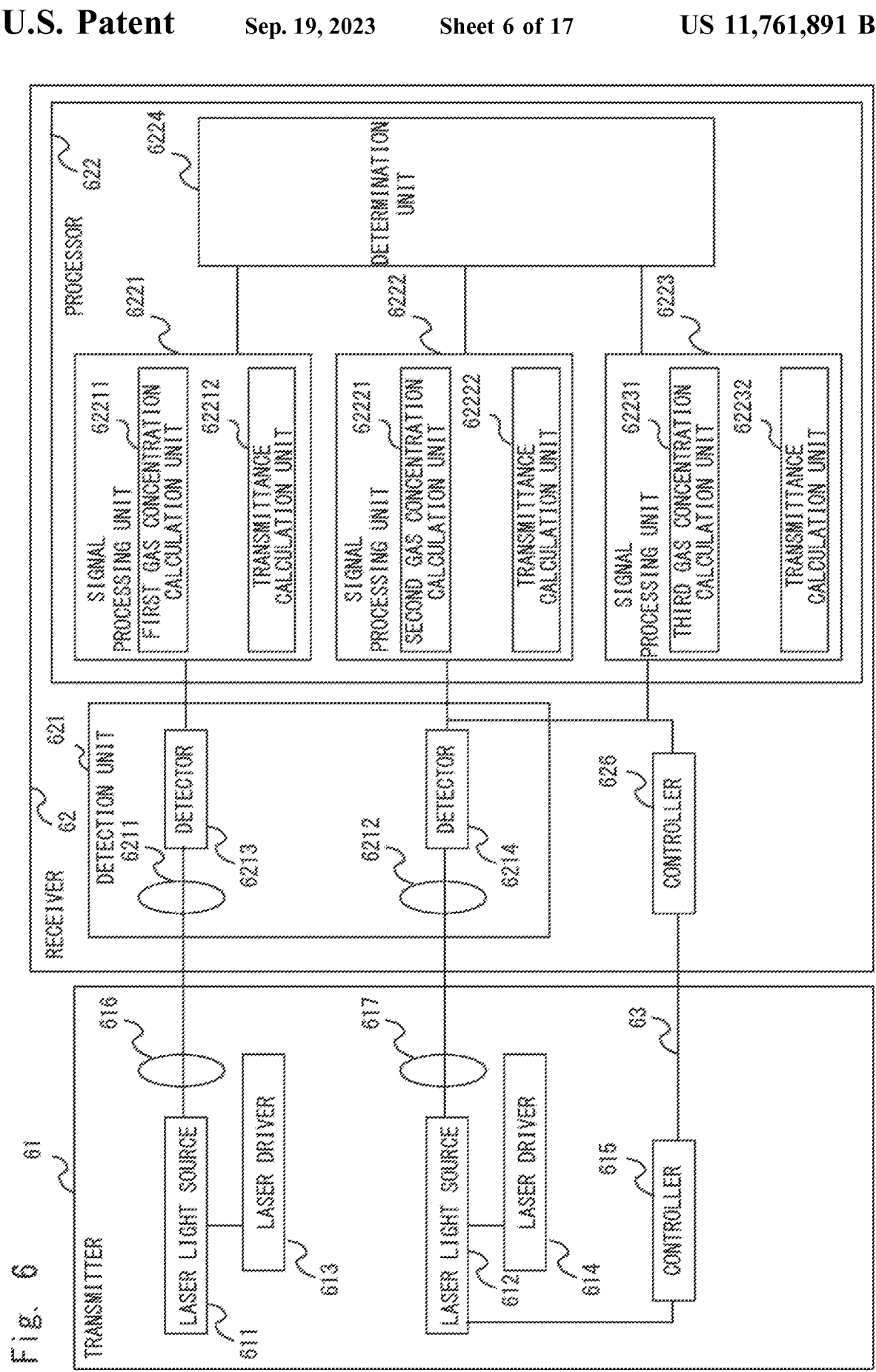
FIG. 6 is a configuration diagram of a fire detection system according to a fourth example embodiment.
Figure 9:
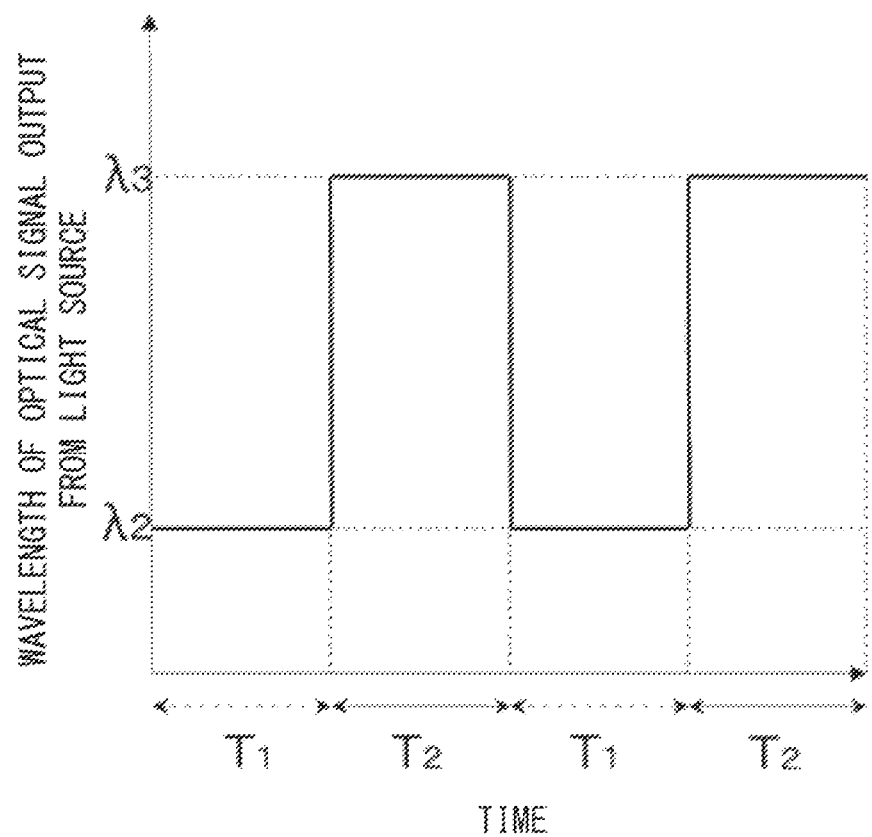
FIG. 9 is a diagram showing a relationship between a wavelength and time of an optical signal output from a laser light source according to the fourth example embodiment.

Referring next to FIGS. 6 and 9, a fourth example embodiment will be described. In the second example embodiment, the concentrations of the three types of gas and the transmittances have been calculated using the three light sources and the progress of the fire has been determined based on them. In this example embodiment, the output wavelength of one of two light sources is switched at regular time intervals, the concentrations of the three types of gas and the transmittances are calculated, thereby determining a fire, a sign of a normal fire, or a non-fire.

Configurations of Example Embodiment

FIG. 6 shows a block diagram showing a configuration of a fire detection system according to this example embodiment. A transmitter (61) includes laser light sources (611 and 612), laser drivers (613 and 614), a controller (615), and condensers (616 and 617). The laser light sources (611 and 612) output optical signals. The condensers (616 and 617) convert optical signals output from the laser light sources (611 and 612) into quasi-parallel light beams. Further, the condensers (616 and 617) transmit the optical signals converted into the quasi-parallel light beams to a receiver (62).

The receiver (62) includes a detection unit (621), signal processing units (6221, 6222, and 6223), a determination unit (6224), and a controller (626). The signal processing units (6221, 6222, and 6223), the determination unit (6224), and the controller (626) may be software or modules whose processing is executed by a processor (622) executing a program stored in a memory. Alternatively, the signal processing units (6221, 6222, and 6223), the determination unit (6224), and the controller (626) may be hardware such as circuits or chips.

The detection unit (621) condenses the received optical signals using condensers (6211 and 6212). Detectors (6213 and 6214) receive the optical signals condensed in the condensers (6211 and 6212) and convert the received optical signals into electric signals. The detectors (6213 and 6214) may be software or modules whose processing is executed by the processor (622) executing a program stored in a memory. Alternatively, the detectors (6213 and 6214) may be hardware such as circuits or chips. Further, the detectors (6213 and 6214) may be software or modules whose processing is executed by a processor other than the processor (622) executing a program stored in a memory.

The signal processing units (6221, 6222, and 6223) respectively include gas concentration calculation units (62211, 62221, and 62231) and transmittance calculation units (62212, 62222, and 62232). The gas concentration calculation unit (62211) calculates a gas concentration using the electric signal generated in the detector (6213). The transmittance calculation unit (62212) calculates a transmittance using the electric signal generated in the detector (6213). The gas concentration calculation units (62221 and 62231) calculate the gas concentration using the electric signal generated in the detector (6214). The transmittance calculation units (62222 and 62232) calculate the transmittance using the electric signal generated in the detector (6214). The transmittance is a rate of decrease of the optical signal from the state in which there is no smoke whose intensity is in a wavelength range around the absorption peak. The time in the controller (615) and that in the controller (626) are synchronized with each other. The controller (615) transmits a switch signal to the controller (626) at a timing when the wavelength of the optical signal output from the laser light source (612) is switched. Upon receiving the switch signal, the controller (626) changes the destination of the electric signal output from the detector (6214). The wired cable (63) connects the controller (615) and the controller (626). The determination unit (6224) determines the progress of the fire from the gas concentration and the transmittance that have been calculated. Since the transmittance is similarly reduced by smoke in any optical signal used in this example embodiment, the transmittance used in the determination unit (6224) may be any one of the three values calculated in the transmittance calculation units (62212, 62222, and 62232).

Operations of Example Embodiment

Referring next to FIG. 9, a relation between the wavelength of the optical signal output from the laser light source and time will be described. The laser driver (613) controls a drive current and a temperature of the optical signal output from the laser light source (611). The laser light source (611) outputs the optical signal with a wavelength λ1 μm. The condenser (616) converts the optical signal output from the laser light source (611) into a quasi-parallel light beam. The optical signal converted into the quasi-parallel light beam propagates through the measurement target space and is transmitted to the receiver (62).

The condenser (6211) condenses the received optical signal and outputs the condensed optical signal to the detector (6213). The detector (6213) receives the optical signal and converts the received optical signal into an electric signal. The detector (6213) outputs the electric signal to the signal processing unit (6221).

The first gas concentration calculation unit (62211) and the transmittance calculation unit (62212) calculate, from the change in the intensity of the optical signal, the average carbon dioxide (CO2) concentration and the average transmittance in the wavelength of λ1 μm in the section between the transmitter (61) and the receiver (62).

When the time is a period T1, the controller (615) causes the laser light source (612) whose drive current and temperature have been controlled by the laser driver (614) to output an optical signal with a wavelength λ2 μm. The condenser (617) converts the optical signal output from the laser light source (612) into a quasi-parallel light beam. The optical signal converted into the quasi-parallel light beam propagates through the measurement target space and is transmitted to the receiver (62).

The condenser (6212) condenses the received optical signal and outputs the condensed optical signal to the detector (6214). The detector (6214) receives the optical signal and converts the received optical signal into an electric signal. The detector (6214) outputs the electric signal to the signal processing unit (6222).

The second gas concentration calculation unit (62221) and the transmittance calculation unit (62222) calculate the average carbon monoxide (CO) concentration and the average transmittance in the wavelength of λ2 μm in the section between the transmitter (61) and the receiver (62) from the change in the intensity of the optical signal.

When the time is a period T2, the controller (615) causes the laser light source (612) whose drive current and temperature have been controlled by the laser driver (614) to output an optical signal with a wavelength λ3 μm. The condenser (617) converts the optical signal output from the laser light source (612) into a quasi-parallel light beam. The optical signal converted into the quasi-parallel light beam propagates through the measurement target space and is transmitted to the receiver (62).

The condenser (6212) condenses the received optical signal and outputs the condensed optical signal to the detector (6214). The detector (6214) receives the optical signal and converts the received optical signal into an electric signal. The detector (6214) outputs the electric signal to the signal processing unit (6223).

The third gas concentration calculation unit (62231) and the transmittance calculation unit (62232) calculate the average water vapor (H2O) concentration and the average transmittance in the wavelength of λ3 μm in the section between the transmitter (61) and the receiver (62) from the change in the intensity of the optical signal.

The controller (615) and the controller (626) switch T1 and T2 at regular time intervals and are synchronized via a wired cable (63). The symbol λ1 denotes a wavelength included in an absorption band of CO2 molecules, λ2 denotes a wavelength included in an absorption band of CO molecules, and λ3 denotes a wavelength included in an absorption band of H2O molecules.

FIG. 10 shows a schematic view of a change in the transmittance over time in the event of a normal fire and a non-fire. Further, FIG. 11 shows a schematic view of a change in the CO2 concentration over time in the event of a fire and a non-fire. Further, FIG. 12 shows a schematic view of a change in the H2O concentration over time in the event of a fire and a non-fire. Further, FIG. 13 shows a schematic view of a change in the CO/CO2 concentration ratio over time in the event of a fire and a non-fire. Further, FIG. 15 shows a schematic view of the change in the transmittance over time in the event of an alcohol fire and a non-fire.

Compared to the case in the event of a non-fire, in the event of a normal fire, the transmittance is decreased and the gas concentration is increased. When it has been determined that there is a fire in both the change in the gas concentration and the change in the transmittance, the determination unit (6224) determines that a fire is occurring and issues an alert. As shown in FIG. 13, the rate of rise of the CO/CO2 concentration ratio is higher than those of other gases. When it has been determined, by using the above results, that there is a fire in both the change in the CO/CO2 concentration ratio and the change in the transmittance, the determination unit (6224) determines that the current state is a smoked state and calls attention for a fire. As shown in FIG. 15, in the event of an alcohol fire, the transmittance is not reduced. Therefore, when the transmittance is not reduced, the determination unit (6224) determines that an alcohol fire is occurring when it has been determined that a fire is occurring in both the change in the concentration of carbon dioxide and the change in the concentration of water vapor, both of which being generated in the event of an alcohol fire.

Effects of Example Embodiment

According to this example embodiment, effects similar to those in the third example embodiment may be obtained.

Figure 7:
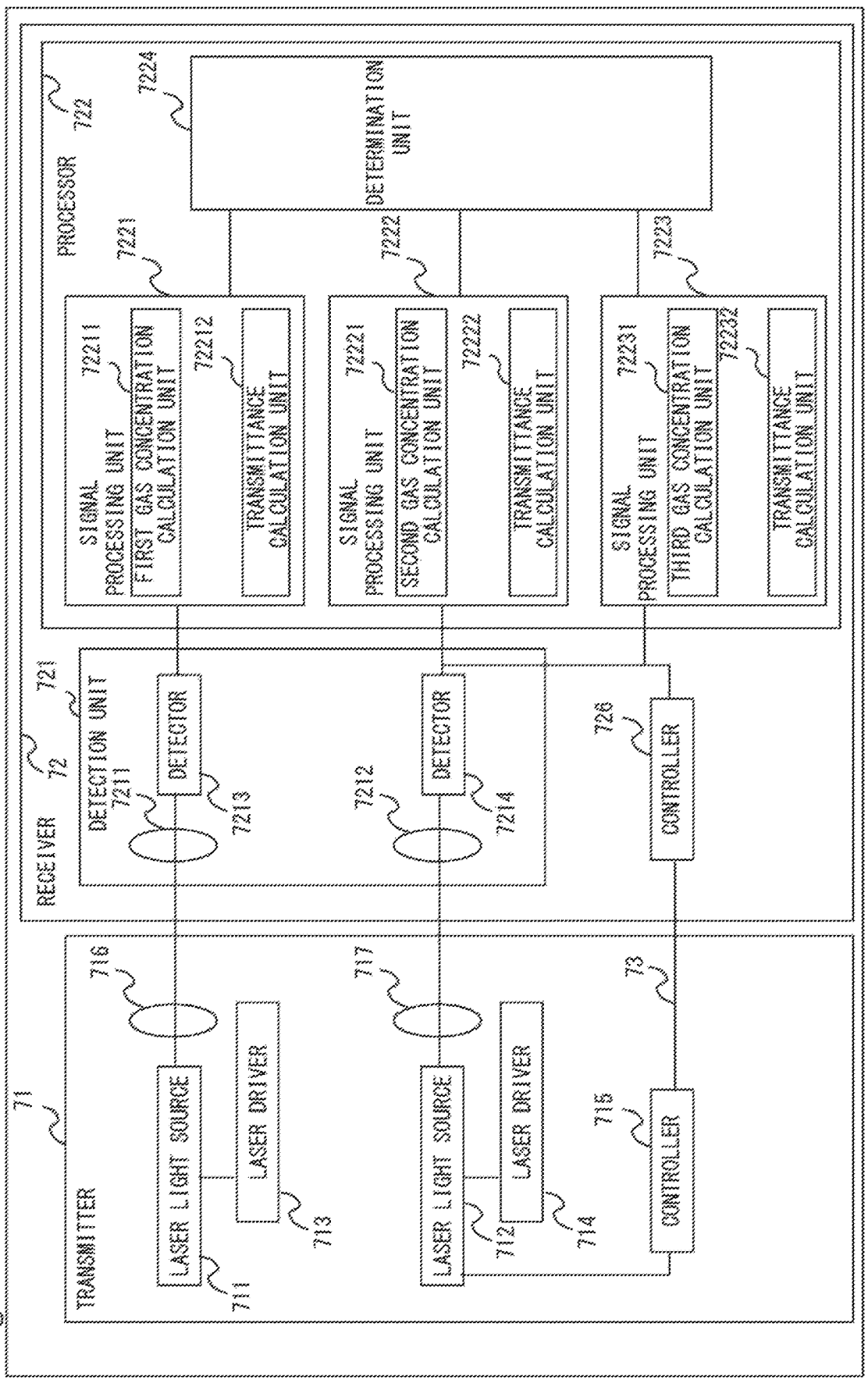
FIG. 7 is a configuration diagram of the fire detection system according to the fourth example embodiment.
Figure 8:
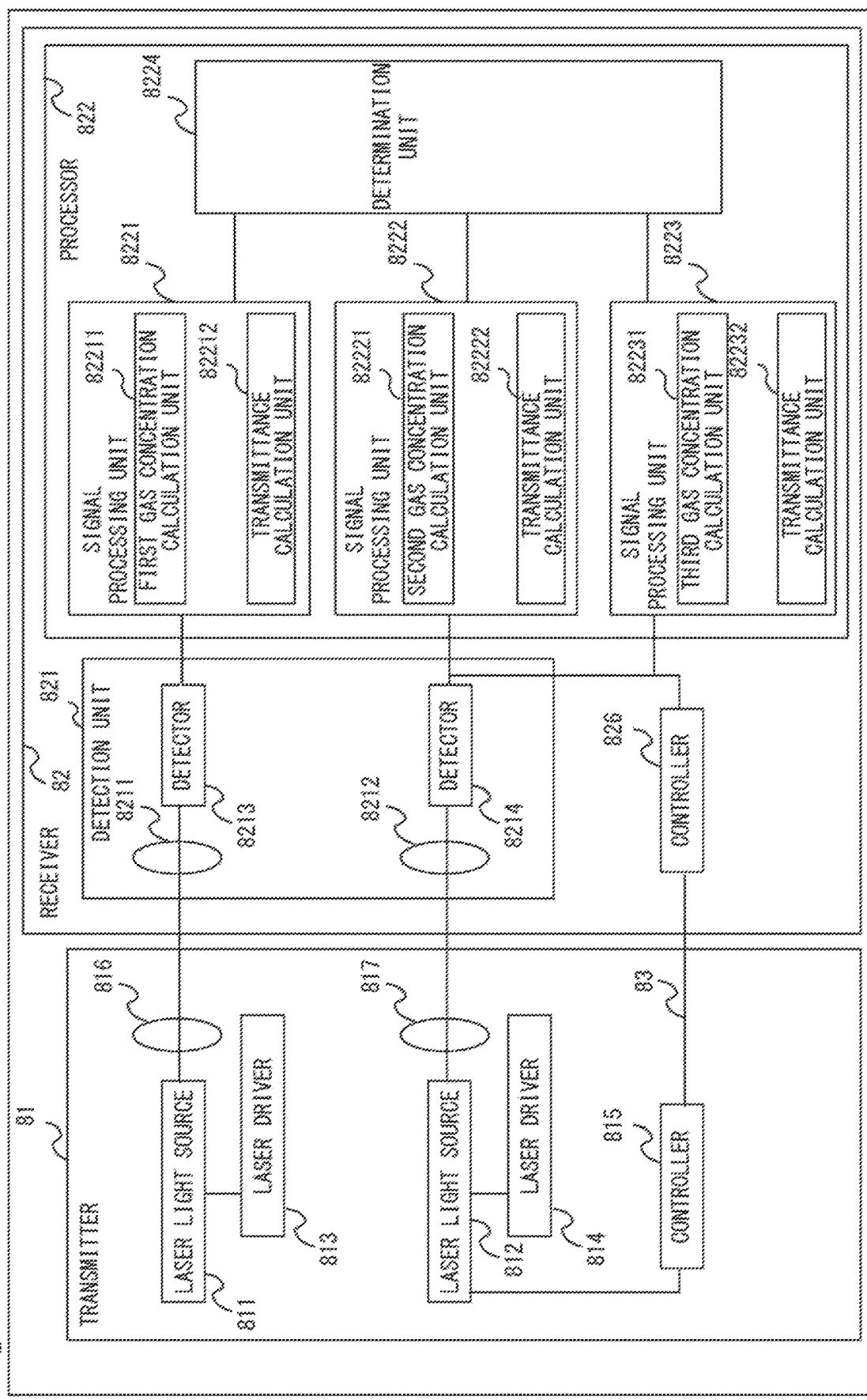
FIG. 8 is a configuration diagram of the fire detection system according to the fourth example embodiment.

The contents of this example embodiment are not limited to the aforementioned description. In the aforementioned description, the example in which the optical signal with a wavelength λ1 µm is output from the laser light source (611) and the wavelength of the optical signal output from the laser light source (612) is switched to λ2 µm or λ3 µm at regular time intervals has been described. Alternatively, as shown in FIG. 7, an optical signal with a wavelength λ2 µm may be output from a laser light source (711) and the wavelength of an optical signal output from a laser light source (712) may be switched to λ1 µm and λ3 µm at regular time intervals. Further, as shown in FIG. 8, an optical signal with a wavelength λ3 µm may be output from a laser light source (811) and the wavelength of an optical signal output from a laser light source (812) may be switched to λ1 µm and λ2 µm at regular time intervals.

Further, in the aforementioned description, the determination unit (6224) evaluates, as an index of the determination, whether the transmittance is below the threshold. Alternatively, the determination unit (6224) may evaluate whether the smoke concentration Cs calculated based on the following expression exceeds a threshold.

$$I_s = I_o \times e^{-CsD} \quad (1)$$

Here, Io denotes an intensity of the optical signal output from the transmitter (61), Is denotes an intensity of the optical signal received by the receiver (62), and D denotes a distance between the transmitter (61) and the receiver (62).

Further, while the example in which the transmitter (61) and the receiver (62) are used to be separated from each other has been described in the aforementioned description, the transmitter/receiver (31) in which the transmitter and the receiver are integrally formed may be used, as shown in FIG. 3. The optical signal output from the transmitter/receiver (31) may be reflected in the direction of the transmitter/receiver (31) using the reflector (32) and the reflected optical signal may be received by the transmitter/receiver (31). According to this configuration, the number of devices that require power feeding can be limited to one, the number of devices that require anti-explosion measures may be reduced, there is no need to synchronize the controllers, and the wired cable may be removed.

Further, the wired cable for synchronization of the controller (615) and the controller (626) may be changed to a wireless connection. According to this configuration, the wired cable may be removed. At this time, the optical signal output from the transmitter/receiver (31) may be reflected a plurality of times and the reflected optical signal may be received by the transmitter/receiver (31), and the propagation distance may thus be increased. According to this configuration, the degree of accuracy of the measurement can be improved.

Further, while the example in which the signal processing unit is divided into three parts has been described in the aforementioned description, two of the three parts may be formed as one signal processing unit or all the three parts may be formed as one signal processing unit.

Further, in the aforementioned description, it is evaluated whether the concentration ratio of carbon monoxide to carbon dioxide exceeds a threshold as an index for judging the sign of a normal fire. Alternatively, it may be evaluated whether the concentration of carbon monoxide exceeds a threshold instead of calculating the ratio. According to this configuration, the processing may be simplified.

Further, while the example in which the three transmittances are calculated and used based on the three optical signals has been described in the aforementioned description, the three transmittances may be averaged or two of the three transmittances may be averaged to improve the accuracy. Alternatively, the system may be simplified using only one of the three transmittances. Further alternatively, a new light source may be introduced and the transmittance may be calculated based on the output optical signal.

Fifth Example Embodiment

Figure 16:
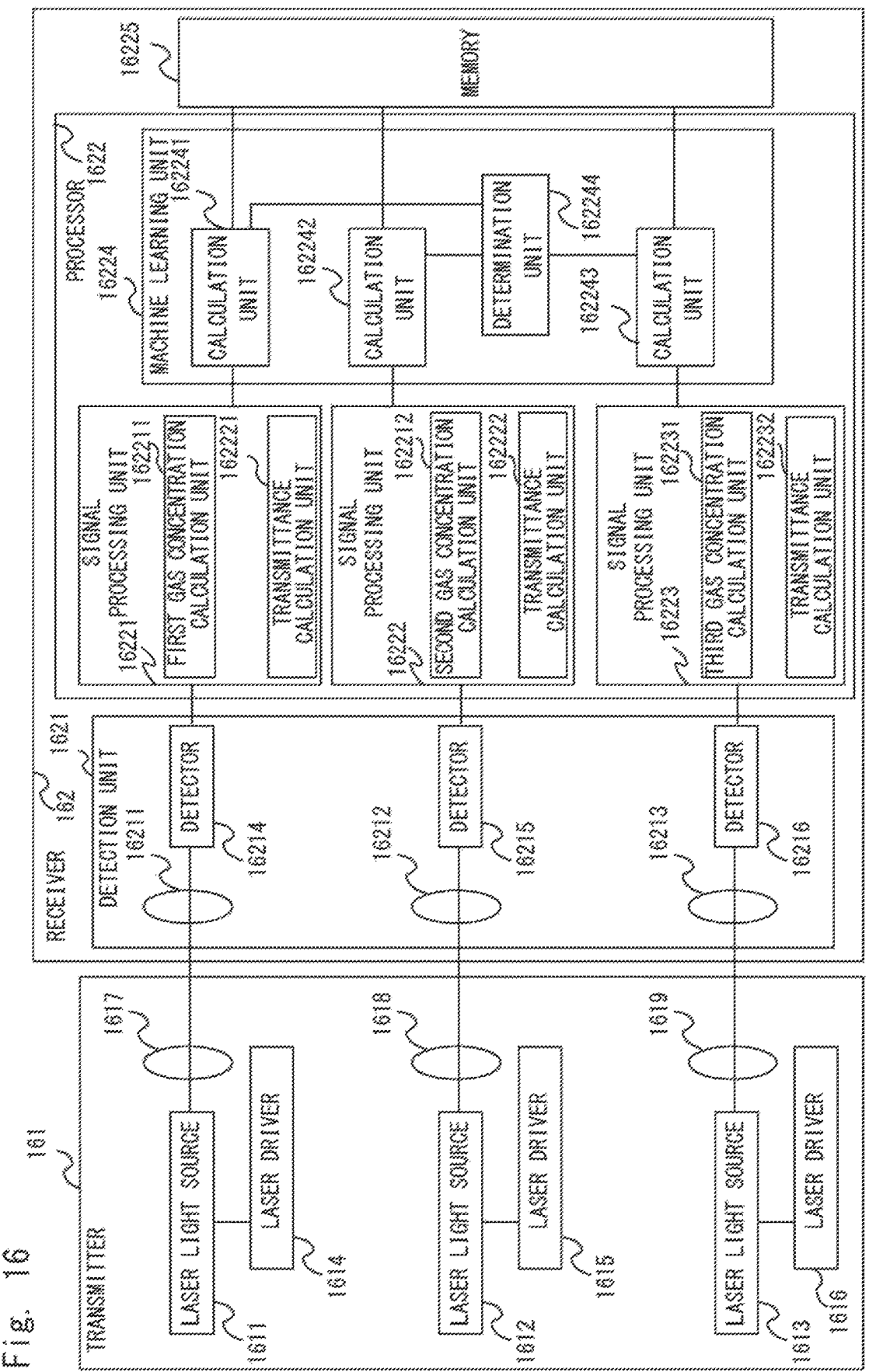
FIG. 16 is a configuration diagram of a fire detection system according to a fifth example embodiment.

Referring next to FIG. 16, a fifth example embodiment of the present application will be described. In the second, third, and fourth example embodiments, the progress of the fire has been determined by comparing the concentrations of the three types of gas and the transmittances with thresholds. In this example embodiment, a large number of patterns of the changes in the concentration of the gas that is generated at a time of fire and the changes in transmittance and the changes in the concentration of the gas at a time of non-fire and the changes in the transmittance are learned and the patterns of the changes in the gas concentration and the transmittance that are being measured are compared with the learned patterns, whereby the progress of the fire is determined.

Configurations of Example Embodiment

FIG. 16 shows a block diagram showing a configuration of a fire detection system according to this example embodiment. A transmitter (161) includes laser light sources (1611, 1612, and 1613), laser drivers (1614, 1615, and 1616), and condensers (1617, 1618, and 1619). The three laser light sources (1611, 1612, and 1613) output three optical signals. The three condensers (1617, 1618, and 1619) convert the optical signals output from the laser light sources (1611, 1612, and 1613) into quasi-parallel light beams. Further, the three condensers (1617, 1618, and 1619) transmit the optical signals converted into the quasi-parallel light beams to a receiver (162).

The receiver (162) includes a detection unit (1621), signal processing units (16221, 16222, and 16223), and a machine learning unit (16224). The signal processing units (16221, 16222, and 16223) and the machine learning unit (16224) may be software or modules whose processing is executed by the processor (1622) executing a program stored in a memory. Alternatively, the signal processing units (16221, 16222, and 16223) and the machine learning unit (16224) may be hardware such as circuits or chips.

The detection unit (1621) condenses the three received optical signals by three respective condensers (16211, 16212, and 16213). Then these optical signals are received by three detectors (16214, 16215, and 16216) and then converted into electric signals.

The signal processing units (16221, 16222, and 16223) respectively include gas concentration calculation units (162211, 162221, and 162231) and transmittance calculation units (162212, 162222, and 162232). The gas concentration calculation units (162211, 162221, and 162231) calculate the gas concentrations using the electric signals generated in the detectors (16214, 16215, and 16216). The transmittance calculation units (162212, 162222, and 162232) calculate the transmittances using the electric signals generated in the detectors (16214, 16215, and 16216). The transmittance is a rate of decrease of the optical signal from the state in which there is no smoke whose intensity is in a wavelength range around the absorption peak. At the time of learning, the machine learning unit (16224) causes a memory (16225) to accumulate the changes in the gas concentration and the transmittance that have been calculated. Further, calculation units (162241, 162242, and 162243) learn the patterns of the changes in the gas concentration and the transmittance accumulated in the memory (16225). The calculation units (162241, 162242, and 162243) store the results of the learning in the memory (16225). At the time of operation, the calculation units (162241, 162242, and 162243) perform calculations from the patterns of the changes in the gas concentration and the transmittance that have been calculated and the results of the learning stored in the memory (16225) and the determination unit (162244) determines whether a fire is occurring or not by machine learning. Since the transmittance is similarly reduced by smoke in any optical signal used in this example embodiment, the transmittances accumulated at the time of learning and the transmittance used for the calculation at the time of operation may be any one of the three values calculated in the transmittance calculation units (162212, 162222, and 162232).

Operations of Example Embodiment

Next, operations regarding the transmitter (161) and the receiver (162) will be described. The laser driver (1614) controls a drive current and a temperature of the optical signal output from the laser light source (1611). The laser light source (1611) outputs an optical signal with a wavelength $\lambda 1$ μm. The condenser (1617) converts the optical signal output from the laser light source (1611) into a quasi-parallel light beam. The optical signal converted into the quasi-parallel light beam propagates through the measurement target space and is transmitted to the receiver (162).

The condenser (16211) condenses the received optical signal and outputs the condensed optical signal to the detector (16214). The detector (16214) receives the optical signal and converts the received optical signal into an electric signal. The detector (16214) outputs the electric signal to the signal processing unit (16221).

The first gas concentration calculation unit (162211) and the transmittance calculation unit (162212) calculate, from the change in the intensity of the optical signal, an average carbon dioxide ($CO_2$) concentration and an average transmittance in the wavelength of $\lambda 1$ μm in the section between the transmitter (161) and the receiver (162).

The laser driver (1615) controls a drive current and a temperature of the optical signal output from the laser light source (1612). The laser light source (1612) outputs an optical signal with a wavelength $\lambda 2$ μm. The condenser (1618) converts the optical signal output from the laser light source (1612) into a quasi-parallel light beam. The optical signal converted into the quasi-parallel light beam propagates through the measurement target space and is transmitted to the receiver (162).

The condenser (16212) condenses the received optical signal and outputs the condensed optical signal to the detector (16215). The detector (16215) receives the optical signal and converts the received optical signal into an electric signal. The detector (16215) outputs the electric signal to the signal processing unit (16222).

The second gas concentration calculation unit (162221) and the transmittance calculation unit (162222) calculate, from the change in the intensity of the optical signal, the average carbon monoxide (CO) concentration and the average transmittance in the wavelength of $\lambda 2$ μm in the section between the transmitter (161) and the receiver (162).

The laser driver (1616) controls a drive current and a temperature of the optical signal output from the laser light source (1613). The laser light source (1613) outputs an optical signal with a wavelength $\lambda 3$ μm. The condenser (1619) converts the optical signal output from the laser light source (1613) into a quasi-parallel light beam. The optical signal converted into the quasi-parallel light beam propagates through the measurement target space and is transmitted to the receiver (162).

The condenser (16213) condenses the received optical signal and outputs the condensed optical signal to the detector (16216). The detector (16216) receives the optical signal and converts the received optical signal into an electric signal. The detector (16216) outputs the electric signal to the signal processing unit (16233).

The third gas concentration calculation unit (162231) and the transmittance calculation unit (162232) calculate the average water vapor ($H_2O$) concentration and the average transmittance in the wavelength of $\lambda 3$ μm in the section between the transmitter (161) and the receiver (162) from the change in the intensity of the optical signal. Note that $\lambda 1$ denotes a wavelength included in the absorption band of $CO_2$ molecules, $\lambda 2$ denotes a wavelength included in the absorption band of CO molecules, and $\lambda 3$ denotes a wavelength included in the absorption band of $H_2O$ molecules.

This example embodiment may be divided into a learning stage in which a model for determining a fire or a non-fire is constructed and an operation stage for determining a fire or a non-fire from changes in the gas concentration and the transmittance that have been calculated. At the time of learning, the changes in the gas concentration and the transmittance that have been calculated are accumulated in the memory (16225). Further, the changes in the gas concentration and the transmittance in the event of a fire are calculated independently from the changes in the gas concentration and the transmittance in the event of non-fire and are accumulated in the memory (16225). For example, the changes in the gas concentration and the transmittance in the event of a fire may be calculated using a simulation or may be calculated using the gas concentration, the transmittance and the like calculated when a fire has actually occurred. The calculation units (162241, 162242, and 162243) learn the accumulated patterns of the changes in the gas concentration and the transmittance. The results of the learning derived by the calculation are stored in the memory (16225) as a model constructed by extracting the feature amounts at a time of fire and non-fire. At the time of operation, the calculation units (162241, 162242, and 162243) perform calculation using the results of the learning stored in the memory (16225) and the changes in the gas concentration and the transmittance that have been calculated. The calculation units (162241, 162242, and 162243) calculate the likelihood of a fire and the likelihood of a non-fire. The determination unit (162244) determines that a fire is occurring when the likelihood of a fire is larger than the likelihood of a non-fire. Otherwise the determination unit (162244) determines that there is no fire.

FIG. 10 shows a schematic view of the change in the transmittance over time in the event of a normal fire and a non-fire. Further, FIG. 11 shows a schematic view of the change in the CO2 concentration over time in the event of a fire and a non-fire. Further, FIG. 12 shows a schematic view of the change in the H2O concentration over time in the event of a fire and a non-fire. Further, FIG. 13 shows a schematic view of the change in the CO/CO2 concentration ratio over time in the event of a fire and a non-fire. Further, FIG. 15 shows a schematic view of the change in the transmittance over time in the event of an alcohol fire and a non-fire.

Compared to the case in the event of a non-fire, in the event of a normal fire, the transmittance is decreased and the gas concentration is increased. When it has been determined that there is a fire in both the change in the water vapor concentration and the change in the transmittance, the machine learning unit (162241) determines that a fire is occurring and issues an alert. As shown in FIG. 13, the rate of rise of the CO/CO2 concentration ratio is higher than those of other gases. When it has been determined, by using the above results, that a fire is occurring in both the change in the CO/CO2 concentration ratio and the change in the transmittance, the machine learning unit (162241) determines that the current state is a smoked state and calls attention for a fire. As shown in FIG. 15, in the event of an alcohol fire, the transmittance is not reduced. Therefore, when the transmittance is not reduced, the machine learning unit (162241) determines that an alcohol fire is occurring when it is determined that a fire is occurring from both the change in the carbon dioxide concentration and the change in the water vapor concentration, which are generated also when an alcohol fire occurs.

Effects of Example Embodiment

Figure 14:
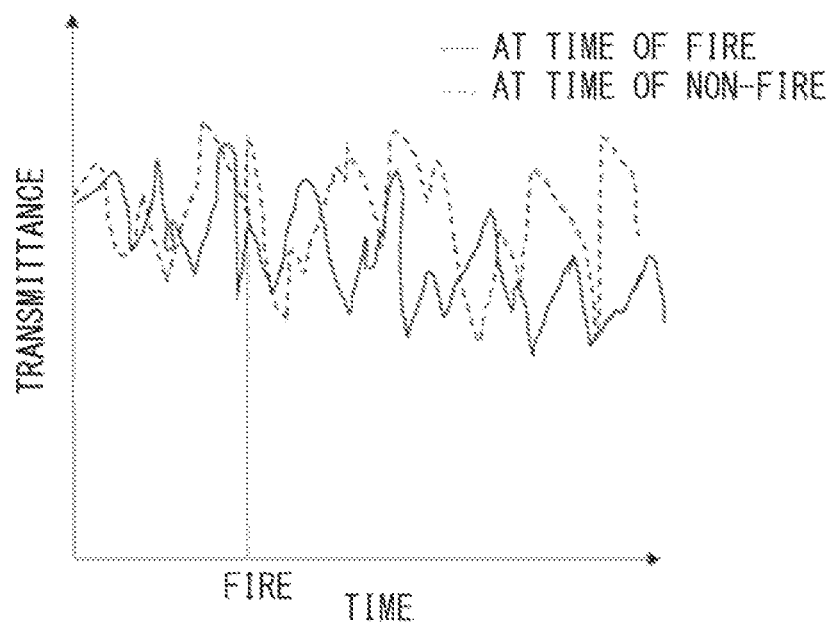
FIG. 14 is a schematic view of a change in the transmittance of a fire and a non-fire when noise is large.

According to this example embodiment, besides the effects described in the second example embodiment, the following effects may be obtained. Specifically, it is possible to determine the progress of the fire even when the threshold cannot be set. FIG. 14 shows a graph showing changes in the transmittance of a fire and a non-fire when noise is large. As shown in FIG. 14, when the noise is larger than the amount of decrease in the transmittance in the event of a fire, the threshold cannot be appropriately set. In this example embodiment, even in this case, the progress of the fire can be captured by machine learning a large amount of accumulated information.

The contents of the present application are not limited to those in the aforementioned description. In the aforementioned description, the determination unit (162244) evaluates the reduction in the transmittance as the index of the determination. Alternatively, the determination unit (162244) may evaluate whether the smoke concentration Cs calculated based on the following expression exceeds a threshold.

$$I_s = I_o \times e^{-CsD} \quad (1)$$

Here, Io denotes an intensity of the optical signal output from the transmitter (161), Is denotes an intensity of the optical signal received by the receiver (162), and D denotes a distance between the transmitter (161) and the receiver (162).

Further, while the example in which the transmitter (161) and the receiver (162) are separately used has been described in the aforementioned description, the transmitter/receiver (31) in which the transmitter and the receiver are integrally formed may be used, as shown in FIG. 3. The optical signal output from the transmitter/receiver (31) may be reflected in the direction of the transmitter/receiver (31) using the reflector (32) and the reflected optical signal may be received by the transmitter/receiver (31). According to this configuration, the number of devices that require power feeding is one and the number of devices that require anti-explosion measures may be reduced.

The optical signal output from the transmitter/receiver (31) may be reflected a plurality of times and the reflected optical signal may be received by the transmitter/receiver (31), and the propagation distance may thus be increased. According to this configuration, the degree of accuracy of the measurement can be improved.

Further, while the example in which the signal processing unit is divided into three parts has been described in the aforementioned description, two of the three parts may be formed as one signal processing unit or the three parts may be formed as one signal processing unit.

Further, while the concentration ratio of carbon monoxide to carbon dioxide is evaluated as an index for determining whether there is a sign of a fire in the aforementioned description, the concentration of carbon monoxide may be evaluated instead of calculating the ratio. According to this configuration, the processing may be simplified.

Further, while the example in which the three transmittances are calculated and used based on the three optical signals has been described in the aforementioned description, the three transmittances may be averaged or two of the three transmittances may be averaged to improve the accuracy, or the system may be simplified using only one of the three transmittances. Further, a new light source may be introduced and the transmittance may be calculated based on the output optical signal.

In the aforementioned examples, the program(s) can be stored and provided to a computer using any type of non-transitory computer readable media. Non-transitory computer readable media include any type of tangible storage media. Examples of non-transitory computer readable media include magnetic storage media (such as flexible disks, magnetic tapes, hard disk drives, etc.), optical magnetic storage media (e.g., magneto-optical disks). Examples of non-transitory computer readable media further include CD-Read Only Memory (ROM), CD-R, and CD-R/W. Examples of non-transitory computer readable media further include semiconductor memories. The semiconductor memories include, for example, mask ROM, Programmable ROM (PROM), Erasable PROM (EPROM), flash ROM, Random Access Memory (RAM), etc.). The program(s) may be provided to a computer using any type of transitory computer readable media. Examples of transitory computer readable media include electric signals, optical signals, and electromagnetic waves. Transitory computer readable media can provide the program to a computer via a wired communication line (e.g., electric wires, and optical fibers) or a wireless communication line.

INDUSTRIAL APPLICABILITY

The present disclosure can be applied to fire detection in a wide area. In particular, the present disclosure can be applied to fire detection in scenes such as tunnels on roads where there are changes such as gas, smoke concentration, temperature, or humidity due to various external factors and where there are large environmental changes other than a fire.

The present disclosure is not limited to the aforementioned example embodiments and may be changed as appropriate without departing from the spirit of the present disclosure.

The whole or a part of the exemplary embodiments disclosed above can be described as, but not limited to, the following supplementary notes.

(Supplementary Note 1)

A receiver comprising:

a detection unit comprising a sensor configured to receive a first optical signal of a wavelength included in an absorption band of water molecules and a second optical signal of a wavelength included in an absorption band of carbon dioxide molecules;

a signal processing unit configured to calculate a water vapor concentration and a carbon dioxide concentration from changes in intensities of the first and second optical signals; and a determination unit configured to determine whether or not there is a fire that is caused by alcohol combustion based on the water vapor concentration and the carbon dioxide concentration.

(Supplementary Note 2)

The receiver according to Supplementary Note 1, wherein the detection unit further comprises a sensor configured to receive a third optical signal of a wavelength included in an absorption band of carbon monoxide molecules, the signal processing unit calculates a carbon monoxide concentration from the change in the intensity of the third optical signal and calculates a transmittance of at least one of the first to third optical signals, and the determination unit determines a sign of a fire based on the carbon monoxide concentration when the calculated transmittance is lower than a predetermined threshold.

(Supplementary Note 3)

The receiver according to Supplementary Note 2, wherein the detection unit comprises a sensor that receives the first optical signal, the second optical signal, and the third optical signal, the signal processing unit comprises a gas concentration calculation unit configured to calculate first to third gas concentrations from the respective intensities of the first to third optical signals and a transmittance calculation unit configured to calculate a transmittance from at least one of the intensities of the first to third optical signals, and the determination unit determines a progress of a fire based on the first to third gas concentrations and the transmittance.

(Supplementary Note 4)

The receiver according to Supplementary Note 3, further comprising:

a memory unit configured to store a feature amount in the event of a fire and a feature amount in the event of a non-fire learned using the first to third gas concentrations and the transmittance as results of learning; and a machine learning unit comprising a determination unit configured to determine the progress of the fire based on results of performing calculations using patterns of the changes in the first to third gas concentrations and the transmittance and the feature amounts.

(Supplementary Note 5)

The receiver according to any one of Supplementary Notes 2 to 4, wherein the determination unit determines that there is a fire based on the carbon dioxide concentration and the water vapor concentration when the calculated transmittance is higher than a predetermined threshold.

(Supplementary Note 6)

A fire detection system comprising:

a receiver comprising a detection unit comprising a sensor configured to receive a first optical signal of a wavelength included in an absorption band of water molecules and a second optical signal of a wavelength included in an absorption band of carbon dioxide molecules, a signal processing unit configured to calculate a water vapor concentration and a carbon dioxide concentration from changes in intensities of the first and second optical signals, and a determination unit configured to determine whether or not there is a fire that is caused by alcohol combustion based on the water vapor concentration and the carbon dioxide concentration; and a transmitter comprising at least one laser light source configured to transmit each of the first and second optical signals to the receiver.

(Supplementary Note 7)

The fire detection system according to Supplementary Note 6, wherein the transmitter comprises a variable wavelength light source configured to transmit the first and second optical signals to the receiver while switching these signals and a controller configured to synchronize a timing of switching the first and second optical signals with the receiver, the receiver comprises a controller configured to synchronize a timing of switching the first and second optical signals with the transmitter and a gas concentration calculation unit configured to calculate first and second gas concentrations from respective intensities of the first and second optical signals, and the gas concentration calculation unit calculates, based on the timing of switching the first and second optical signals, the first gas concentration while the variable wavelength light source is outputting the first optical signal and calculates the second gas concentration while the variable wavelength light source is outputting the second optical signal.

(Supplementary Note 8)

The fire detection system according to Supplementary Note 6 or 7, comprising a transmitter/receiver in which the transmitter and the receiver are integrated and a reflector for reflecting the optical signal output from the transmitter/receiver to the transmitter/receiver, the reflector being arranged so as to sandwich a measurement target space.

(Supplementary Note 9)

A fire detection method executed in a receiver, comprising:

receiving a first optical signal of a wavelength included in an absorption band of water molecules and a second optical signal of a wavelength included in an absorption band of carbon dioxide molecules;

calculating a water vapor concentration and a carbon dioxide concentration from changes in intensities of the first and second optical signals; and determining whether or not there is a fire based on the changes in the water vapor concentration and the carbon dioxide concentration.

(Supplementary Note 10)

The fire detection method according to Supplementary Note 9, comprising:

receiving a third optical signal of a wavelength included in an absorption band of carbon monoxide molecules;

calculating a carbon monoxide concentration from the change in the intensity of the third optical signal and calculating a transmittance of at least one of the first to third optical signals; and determining a sign of a fire based on a carbon monoxide concentration when the calculated transmittance is lower than a predetermined threshold.

(Supplementary Note 11)

The fire detection method according to Supplementary Note 10, comprising:

receiving the first to third optical signals;

calculating first to third gas concentrations from the respective intensities of the first to third optical signals;

calculating a transmittance from the intensity of at least one of the first to third optical signals; and determining a progress of a fire based on the first to third gas concentrations and the transmittance.

(Supplementary Note 12)

The fire detection method according to Supplementary Note 11, comprising:

storing a feature amount in the event of a fire and a feature amount in the event of a non-fire learned using the first to third gas concentrations and the transmittance as results of learning; and determining the progress of the fire based on results of performing calculations using patterns of the changes in the first to third gas concentrations and the transmittance and the feature amounts.

While the present disclosure has been described with reference to the example embodiments, the present disclosure is not limited by the above example embodiments. Various changes that may be understood by those skilled in the art may be made to the configurations and the details of the present disclosure within the scope of the present disclosure.

This application is based upon and claims the benefit of priority from Japanese Patent Application No. 2018-144310, filed on Jul. 31, 2018, the disclosure of which is incorporated herein in its entirety by reference.

REFERENCE SIGNS LIST 21, 41, 61, 71, 81, 161 Transmitter
22, 42, 62, 72, 82, 162 Receiver
211, 212, 213, 411, 611, 612, 711, 712, 811, 812, 1611, 1612, 1613 Laser Light Source
217, 218, 219, 2211, 2212, 2213, 413, 4211, 616, 617, 6211, 6212, 716, 717, 7211, 7212, 816, 817, 8211, 8212, 1617, 1618, 1619, 16211, 16212, 16213 Condenser
214, 215, 216, 412, 612, 614, 713, 714, 813, 814, 1614, 1615, 1616 Laser Driver
221, 421, 621, 721, 821, 1621 Detection Unit
2214, 2215, 2216, 4212, 6213, 6214, 7213, 7214, 8213, 8214, 16214, 16215, 16216 Detector
222, 422, 622, 722, 822, 1622 Processor
2221, 2222, 2223, 4221, 4222, 4223, 6221, 6222, 6223, 7221, 7222, 7223, 8221, 8222, 8223, 16221, 16222, 16223 Signal Processing Unit
16224 Machine Learning Unit
2224, 4224, 6224, 7224, 8224, 162244 Determination Unit
22211, 22221, 22231, 42211, 42221, 42231, 62211, 62221, 62231, 72211, 72221, 72231, 82211, 82221, 82231, 162211, 162221, 162231 Gas Concentration Calculation Unit
22212, 22222, 22232, 42212, 42222, 42232, 62212, 62222, 62232, 72212, 72222, 72232, 82212, 82222, 82232, 162212, 162222, 162232 Transmittance Calculation Unit
162241, 162242, 162243 Calculation Unit
16225 Memory
414, 426, 615, 626, 715, 726, 815, 826 Controller
43, 63, 73, 83 Wired Cable
31 Transmitter/receiver
32 Reflector

What is claimed is:

1. A receiver comprising:
at least one memory storing instructions, and
at least one processor configured to execute the instructions to;
receive a first optical signal of a wavelength included in an absorption band of water molecules and a second optical signal of a wavelength included in an absorption band of carbon dioxide molecules;
calculate a water vapor concentration and a carbon dioxide concentration from changes in intensities of the first and second optical signals;
determine whether or not there is a fire that is caused by alcohol combustion based on the water vapor concentration and the carbon dioxide concentration;
receive a third optical signal of a wavelength included in an absorption band of carbon monoxide molecules;
calculate a carbon monoxide concentration from the change in the intensity of the third optical signal and calculates a transmittance of at least one of the first to third optical signals;
determine a sign of a fire based on the carbon monoxide concentration when the calculated transmittance is lower than a predetermined threshold;
receive the first optical signal, the second optical signal, and the third optical signal;
calculate first to third gas concentrations from the respective intensities of the first to third optical signals;
calculate a transmittance from at least one of the intensities of the first to third optical signals; and
determine a progress of a fire based on the first to third gas concentrations and the transmittance.

2. The receiver according to claim 1, further comprising:
the at least one processor is further configured to execute the instructions to store a feature amount in the event of a fire and a feature amount in the event of a non-fire learned using the first to third gas concentrations and the transmittance as results of learning; and
determine the progress of the fire based on results of performing calculations using patterns of the changes in the first to third gas concentrations and the transmittance and the feature amounts.

3. The receiver according to claim 1, wherein the at least one processor is further configured to execute the instructions to determine that there is a fire based on the carbon dioxide concentration and the water vapor concentration when the calculated transmittance is higher than a predetermined threshold.

4. A fire detection method executed in a receiver, the fire detection method comprising:
receiving a first optical signal of a wavelength included in an absorption band of water molecules and a second optical signal of a wavelength included in an absorption band of carbon dioxide molecules;
calculating a water vapor concentration and a carbon dioxide concentration from changes in intensities of the first and second optical signals;
determining whether or not there is a fire based on the changes in the water vapor concentration and the carbon dioxide concentration;

receiving a third optical signal of a wavelength included in an absorption band of carbon monoxide molecules;

calculating a carbon monoxide concentration from the change in the intensity of the third optical signal and calculating a transmittance of at least one of the first to third optical signals;

determining a sign of a fire based on a carbon monoxide concentration when the calculated transmittance is lower than a predetermined threshold;

receiving the first to third optical signals;

calculating first to third gas concentrations from the respective intensities of the first to third optical signals;

calculating a transmittance from the intensity of at least one of the first to third optical signals; and determining a progress of a fire based on the first to third gas concentrations and the transmittance.

5. The fire detection method according to claim 4, comprising:

storing a feature amount in the event of a fire and a feature amount in the event of a non-fire learned using the first to third gas concentrations and the transmittance as results of learning; and determining the progress of the fire based on results of performing calculations using patterns of the changes in the first to third gas concentrations and the transmittance and the feature amounts.

* * * * *